United States Patent [19]

Carson et al.

[11] Patent Number: 5,698,518

[45] Date of Patent: Dec. 16, 1997

[54] METHOD FOR REGULATING INFLAMMATION AND TUMOR GROWTH WITH CALMODULIN, CALMODULIN ANALOGUES OR CALMODULIN ANTAGONISTS

[75] Inventors: Craig W. Carson, Edmond; Charles T. Esmon; Donald S. Houston, both of Oklahoma City, all of Okla.

[73] Assignee: Oklahoma Medical Research Foundation, Oklahoma City, Okla.

[21] Appl. No.: 220,814

[22] Filed: Mar. 30, 1994

[51] Int. Cl.$^6$ ............... C07K 14/435; C07K 14/525
[52] U.S. Cl. ................... 514/12; 514/21; 930/144
[58] Field of Search .................. 514/12, 21; 930/144

[56] References Cited

U.S. PATENT DOCUMENTS

| | | | |
|---|---|---|---|
| 4,758,559 | 7/1988 | Wasley | 514/221 |
| 4,965,271 | 10/1990 | Mandell | 514/263 |
| 5,034,395 | 7/1991 | Tamada | 514/277 |
| 5,096,906 | 3/1992 | Mandell | 514/263 |
| 5,137,889 | 8/1992 | Tamada | 514/252 |

FOREIGN PATENT DOCUMENTS 0471236  2/1992  European Pat. Off. .

OTHER PUBLICATIONS

Tian et al., "Inhibitory Effects of PKC and CAM on TNF Production," *Acta Pharma Sin,* v. 14, n. 5, pp. 447–449 (1993).

Chan et al., "Calmodulin Inhibitor inhibits TNF Induced Neutrophil Chemilun"*Am. Rev. Resp. Dis.,* v. 141, n. 4, p. 4919 (1990).

Aderka, et al., "lL–6 inhibits lipopolysaccharide–induced tumor necrosis factor production in cultured human monocytes, U937 cells, and in mice," *J Immunology* 143:3517–3523 (1989).

Boynton, et al., "Calmodulin stimulates DNA synthesis by rat liver cells," *Biochem Biophys Research Communications* 95:745–749 (1980).

Carson, et al., "Inducible release of an endothelial cell–specific protein, " *Am J Pathol* 139:199–206 (1991).

Chantry, et al., "Modulation of cytokine production by transforming growth factor–β," *J Immunology* 142:4295–4300 (1989).

Cheung, W.Y. "Calmodulin plays a pivotal roll in cellular regulation," *Science* 207:19–27 (1980).

Crocker, et al., "An extracellular role for calmodulin–like activity in cell proliferation," *Biochem J* 253:877–844 (1988).

Dawson, et al., "Mitogenic role for extracellular calmodulin–like activity in normal human umbilical vein endothelial cells, " *British J Haematology* 82:151–160 (1992).

Dedman, et al., "Calmodulin purification and flourescent labeling," *Methods in Enzymology* 102:1–9 (1983).

Essner, et al., "IL–4 down–regulates IL–1 and TNF gene expression in human monocytes," *J Immunology* 142:3857–3861 (1989).

Fiorentino, et al., "IL–10 inhibits cytokine production by activated macrophages," *J Immunology* 147:3815–3822 (1991).

Goberdhan, et al., "A calmodulin–like protein as an extracellular mitogen for the keratinocyte," *British J Dermatology* 129:678–688 (1993).

Grundmann, et al., "Inhibition of endotoxin–induced macrophage tumor necrosis factor expression by a prostacyclin analogue and its beneficial effect in experimental lipopolysaccharide intoxication," *J Infect Diseases* 165:501–505 (1992).

Hampton, et al., "Recognition and plasma clearance of endotoxin by scavenger receptors," *Nature* 352:342–344 (1991).

Hart, et al., "IL–4 suppresses IL–1β, TNF–α and PGE$_2$ production by human peritoneal macrophages," *Immunology* 72:344–349 (1991).

Ikezawa, et al., "Phosphatidylinositol–specific phospholipase C from *Bacillus cereus* and *Bacillus thuringiensis,*" *Methods of Enzymology* 71:731–741 (1981).

Moore, et al., "Endotoxin enhances tissue factor and suppresses thrombomodulin expression of human vascular endothelium in vitro," *J Clin Invest* 79:124–130 (1987).

Ryan, et al., "Kinins, endothelial cells and calmodulin," *Adv Exp Med Biol* 156:671–679 (1983).

Schindler, et al., "Correlations and interactions in the production of Interleukin–6 (IL–6), IL–1, and tumor necrosis factor (TNF) in human blood mononuclear cells: IL–6 suppresses IL–1 and TNF," *Blood* 75:40–47 (1990).

Kunkel, et al., "Regulation of macrophage tumor necrosis factor production by prostaglandin E$_2$," *Biochem Biophys Research Communications* 137:404–410 (1986).

Mac Neil, et al., "Effects of extracellular calmodulin antagonists on B16 melanoma cell growth," *J Invest Dermatology* 83:15–19 (1984).

Means, et al., "Calmodulin–an intracellular calcium receptor," *Nature* 285:73–77 (1980).

le Vraux, et al., "Inhibition of human moncyte TNF production by adenosine receptor agonists," *Life Sciences* 52:1917–1924(1993).

(List continued on next page.)

*Primary Examiner*—Cecilia J. Tsang
*Assistant Examiner*—Patrick R. Delaney
*Attorney, Agent, or Firm*—Sidley & Austin

[57] ABSTRACT

A method of treating patients to inhibit inflammation is disclosed. In the method, an effective amount of calmodulin, a calmodulin analogue or calmodulin receptor agonist is administered to a patient to inhibit production of tumor necrosis factor and/or augment elastase. In another method, an effective amount of calmodulin antagonist is administered to a patient to stimulate immune response or inhibit elastase release. In another embodiment, a diagnostic test is disclosed to be used on patient blood samples to determine individual propensity to regulate tumor necrosis factor and/or elastase by calmodulin, its analogues or receptor agonists.

3 Claims, 19 Drawing Sheets

OTHER PUBLICATIONS

Yui, et al., "Augmentation and suppression of TNF release from macrophages by inflammatory polymorphonuclear leukocytes," *Microbiol Immunol* 37:801–808 (1993).

Means, et al., "Regulatory functions of calmodulin," *Pharmac Ther* 50:255–270 (1991).

Minty, et al., "Interleukin-13 in a new human lymphokine regulating inflammatory and immune responses," *Nature* 362:248–250 (1993).

Moore, et al. "Tumor necrosis factor leads to the internalization and degradation of thrombomodulin from the surface of bovine aortic endothlial cells in culture," *Blood* 73:159–165 (1989).

METHOD FOR REGULATING INFLAMMATION AND TUMOR GROWTH WITH CALMODULIN, CALMODULIN ANALOGUES OR CALMODULIN ANTAGONISTS

TECHNICAL FIELD OF THE INVENTION

This invention relates to the field of substances which have anti-inflammatory or anti-tumor activity and to diagnostic testing of patients for regulation of tumor necrosis factor and elastase activity.

BACKGROUND OF THE INVENTION

Tumor necrosis factor (TNF) is an important early mediator of inflammatory reactions and has been implicated in diverse inflammatory disease processes such as septic shock, rheumatoid arthritis, graft-versus-host disease, and tumor cachexia. Although the induction of TNF release by inflammatory stimuli such as interleukin-1 (IL-1), interferon gamma, and bacterial endotoxin has been well studied, less is known about the negative regulation of this important inflammatory mediator.

Neutrophils and neutrophil elastase are important in host defense and destruction of foreign tissue or cells. Neutrophil elastase also plays an important role in the destruction of normal tissue in diseases like emphysema and rheumatoid arthritis. However, knowledge concerning the release of elastase from neutrophils is incomplete.

In its best known role, calmodulin is an intracellular calcium binding protein important in transducing calcium signals (Means, et al., "Regulatory functions of calmodulin," *Pharmac. Ther.* 50:255–270 (1991); Means, et al., "Calmodulin-an intracellular calcium receptor." *Nature* 285:73–77 (1980)). Calmodulin is a 16.8 kD protein with two globular ends and a long central alpha-helix (dumbbell-shaped). The two globular ends each contain two calcium-binding "EF hand" structural motifs; thus, calmodulin can bind four $Ca^{++}$ ions. When bound to calcium, calmodulin undergoes a conformational change exposing a hydrophobic patch at both ends of the molecule. This conformational change and exposure of the hydrophobic patch allows calmodulin to bind to target enzymes and express its cofactor activity. Calmodulin acts as a cofactor for many regulatory proteins such as kinases, phosphatases, cyclic nucleotide phosphodiesterases, phospholipase, adenylate cyclase, and $Ca^{++}/Mg^{++}$ ATPase. Calmodulin is highly conserved (all vertebrate calmodulin is reportedly the same). Calmodulin is an abundant protein found in almost all eukaryotic, but not prokaryotic, cells and may be up to 4% of the total cell protein content. Calmodulin may be released when cells are injured or die. Calmodulin is present in serum (4 micrograms/ml) (released from platelets). Calmodulin is released into conditioned media of a variety of cultured cells and has been reported to stimulate proliferation of cultured hepatocytes, melanoma cells, leukemic lymphocytes, and HUVEC (human umbilical vein endothelial cells) (Dawson, et al., "Mitogenic role for extracellular calmodulin-like activity in normal human umbilical vein endothelial cells," *Br. J. Haematol.* 82:151–160 (1992); Crocker, et al., "An extracellular role for calmodulin-like activity in cell proliferation," *Biochem. J.* 253:877–884 (1988)).

Although much research has been conducted on TNF and elastase, there remains a continuing need to elucidate how they are regulated. In addition, research done to date on calmodulin has not linked extracellular calmodulin to TNF or elastase regulation.

It has now been found that extracellular calmodulin inhibits TNF release and facilitates elastase release. From this data, it is claimed that calmodulin, calmodulin analogues and calmodulin receptor agonists are useful agents for regulating the inflammatory process. Calmodulin antagonists, which include calmodulin receptor antagonists and calmodulin-binding molecules, may be used to block the interaction of calmodulin with its receptor, thus providing the opposite effect from calmodulin, its analogues and receptor agonists. Calmodulin may serve as a potent modulator of self-directed inflammation by assisting in the recognition of self vs. non-self as prokaryotes (e.g., bacterial pathogens) do not contain calmodulin. In some situations such as in tumor necrosis, release of extracellular calmodulin may lead to an inappropriate host response and failure of the immune/inflammatory systems to eradicate tumor cells. Further, a diagnostic test has been developed which can discern patient variabilities in TNF inhibition by calmodulin and other substances. This test can be utilized in monitoring individual patients for determining effective therapies, and for predicting efficacy of therapy with extracellular calmodulin, calmodulin analogues or calmodulin receptor agonists on the one hand and calmodulin antagonists on the other. A diagnostic test for elastase has also been developed with similar utility.

SUMMARY OF THE INVENTION

This invention concerns a method for regulating tumor necrosis factor (TNF) production in whole blood with calmodulin, its analogues or receptor agonists.

In another embodiment, calmodulin, its analogues or receptor agonists are used in a method to augment neutrophil elastase release.

In another embodiment, calmodulin antagonists are used in a method to stimulate a patient's immune response.

In another aspect, calmodulin antagonists are used in a method to inhibit elastase release.

In another aspect, this invention concerns a method of testing blood from patients for the ability to inhibit TNF production with exogenous calmodulin, its analogues or receptor agonists.

In yet another aspect, this invention concerns a method for testing blood for elastase release as a measure of host defense responsiveness.

Another aspect concerns a method for testing blood for TNF mRNA inhibition by calmodulin.

Another aspect concerns a method for testing blood for augmentation of TNF release by calmodulin antagonists.

Another aspect concerns a method for testing blood for inhibition of elastase release by calmodulin antagonists.

DETAILED DESCRIPTION

Figure 1:
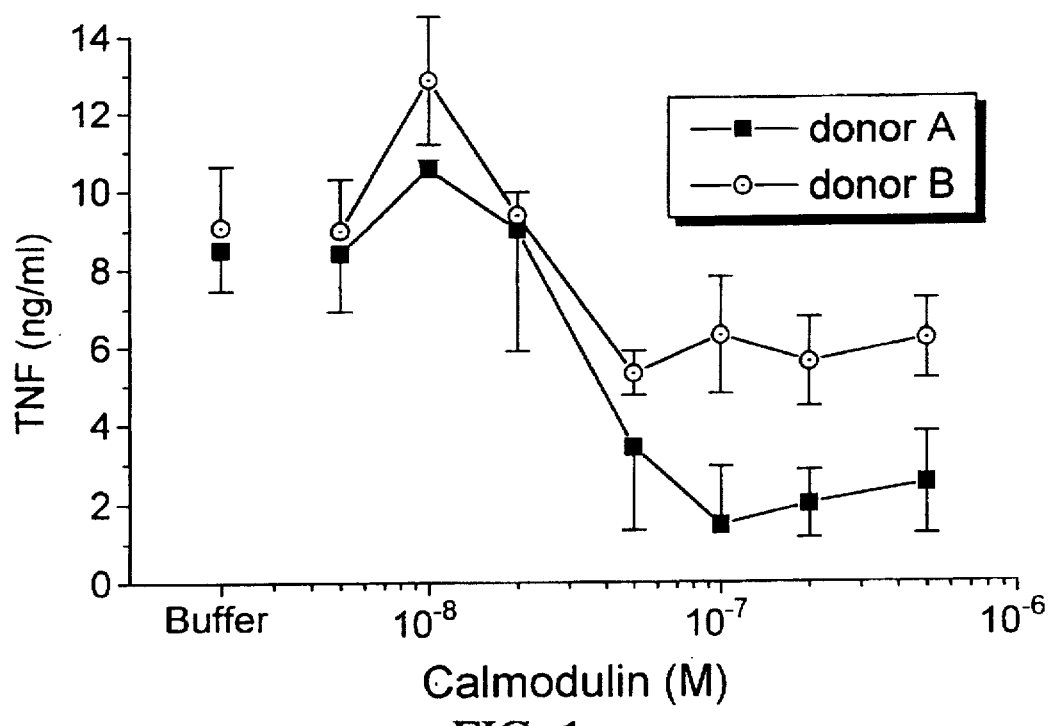
FIG. 1 is a graph depicting the augmentation of elastase release in whole blood by authentic (hog brain) calmodulin.

This invention relates to the use of calmodulin, its analogues or receptor agonists ("calmodulins") to moderate the inflammatory process in which tumor necrosis factor (TNF) is implicated. Calmodulin analogues are defined as calmodulin derivatives or synthetic receptor ligands that mimic the action of calmodulin to inhibit TNF release and to stimulate elastase release. Calmodulin antagonists are substances which block the interaction of calmodulin with its receptor(s) either by binding calmodulin or by blocking its receptor. By administering calmodulin, a calmodulin analogue or a calmodulin receptor agonist to a patient, the amount of TNF produced can be reduced and therefore the inflammation process in which TNF is involved can be reduced as well. Calmodulin antagonists may be used to stimulate the immune response or inhibit elastase release.

In carrying out this invention, calmodulin must first be purified from an appropriate source, or made via any appropriate technique. Calmodulin can be readily produced from any vertebrate tissue. A preferred methodology employs calcium-dependent hydrophobic chromatography on phenyl sepharose as described by Dedman and Kaetzel, *Methods in Enzymology* 102:1–8 (1983) which is herein incorporated by reference. Calmodulin can also be obtained commercially. Bovine testis or brain are the usual sources. Purification methods for calmodulin have been reported in the literature, and any method which will result in calmodulin which will inhibit TNF and augment elastase can be used.

Bovine testis calmodulin can be prepared according to the above identified method. In general, bovine testis obtained from a slaughter house is cut into 2 $cm^2$ pieces and homogenized in 0.15M NaCl, 0.02M Tris-HCl, pH 7.5, 1 mM EDTA in Tris-buffered saline (TBS) (0.02M Tris-HCl, 0.15M NaCl, pH 7.5) using a commercial Waring blender. The resulting homogenate is clarified by centrifugation at 20,000× g for 30 minutes. The supernatant is heated at 90° F. for exactly five minutes using a microwave oven with a temperature probe. The heated extract is immediately cooled on ice and then centrifuged again at 20,000× g for 30 minutes. The resulting supernatant is re-calcified by the addition of $CaCl_2$ to 10 mM after the addition of Tris-HCl, pH 7.5, to 0.05M. The calcified supernatant is applied to a 1.5×10 cm phenyl sepharose column (Pharmacia, Piscataway, N.J.) equilibrated in the same buffer. The column is sequentially washed with 5 mM $CaCl_2$, 0.5M NaCl, 0.02M Tris-HCl, pH 7.5; then 1 mM $CaCl_2$, 0.02M Tris-HCl, pH 7.5; and then eluted with 1 mM EDTA, 0.02M Tris-HCl, pH 7.5, at a flow rate of 2 milliliters/minute, collecting 2 milliliter fractions.

Calmodulin can be administered intravenously (i.v.). In vitro, calmodulin has maximal activity at $1\times10^{-7}$M (1.68 µg/ml) and half-maximal activity at $3\times10^{-8}$M (504 ng/ml). Assuming a plasma volume of 2.45 liters for a 70 kg adult male, approximately 4.1 mg would be given to achieve a plasma concentration of $10^{-7}$M. If calmodulin is distributed in the extracellular space, this would be a volume of approximately 23.3 liters and would require 39 mg to achieve an extracellular volume concentration of $10^{-7}$M. The dose can be adjusted accordingly for plasma volume and patient weight. Calmodulin could be given i.v. to patients with acute inflammation believed to be mediated by TNF such as sepsis or graft vs. host disease. Preferably, calmodulin would be given intravenously for treatment for any disease where an excess of TNF or deficiency of elastase may be involved. Since calmodulin from all vertebrate species is the same, no immune response would be expected if calmodulin, for example, obtained from bovine tissue were administered to humans.

Analogues of calmodulin can be made which exhibit the ability to inhibit TNF and augment elastase release. By mapping the receptor binding site of calmodulin involved in the TNF regulatory process and assessing its conformation, look-alike "mimitope" molecules can be synthesized which will act only on the receptor which mediates the ability of calmodulin to inhibit TNF and augment elastase. It is envisioned that such calmodulin analogues will be used to inhibit inflammation and stimulate neutrophil function (augmentation of elastase) as described above. Such analogues would have the potential advantage of providing oral administration capabilities, and thus would have more potential utility for chronic inflammation such as rheumatoid arthritis or asthma.

It is also envisioned that calmodulin antagonists could be used to moderate TNF production. Such antagonists would bind to calmodulin or its receptors and would be expected to stimulate TNF production if utilized in the method of this invention. Calmodulin antagonists could also be used to restore TNF production in situations where its inhibition by calmodulin is excessive or detrimental as may be the case in tumors. Also, as calmodulin increases elastase release and elastase may in some situations contribute to destruction of normal tissue (e.g., emphysema), calmodulin antagonists may be used to inhibit or antagonize this effect of calmodulin.

In another aspect of the invention, assays have been developed to determine an individual patient's propensity to respond to calmodulin as an inhibitor of TNF or an augmentor of elastase. Such an assay is applicable to testing for response to calmodulin of TNF mRNA or other leukocyte factors. These assays can be used diagnostically to determine appropriate therapy for individual patients.

In the assay, a first and second aliquot of patient's anticoagulated blood are tested with and without a calmodulin source, which can be calmodulin or a cell culture which produces calmodulin. A substance is added to the test well which will either induce TNF release, or stimulate elastase release, or induce some other leukocyte product. The substance that is to be induced or suppressed by calmodulin is then assayed for in the presence and absence of calmodulin.

In a preferred embodiment, ELISA assays have been developed to monitor TNF or elastase amounts.

EXAMPLE 1

Verification of the Identity of Endothelial Calmodulin as an Inhibitor of TNF Calmodulin was isolated from endothelial cells and identified as the agent exhibiting TNF suppression and elastase augmentation according to the following procedure. Human umbilical vein endothelial cells (HUVEC) were isolated and cultured as described in Carson, et al., "Inducible release of an endothelial cell-specific protein," *Am. J. Pathol* 139:199–206 (1991); Moore, et al., "Tumor necrosis factor leads to the internalization and degradation of thrombomodulin from the surface of bovine aortic endothelial cells in culture," *Blood* 73:159–165 (1989); Moore, K. L., "Endotoxin enhances tissue factor and suppresses thrombomodulin expression of human vascular endothelium in vitro," *J. Clin. Invest.* 79:124–130 (1987), which are herein incorporated by reference. For the production of conditioned media, approximately 2 $m^2$ of endothelial cells at first through fourth passage were grown to confluency. After reaching confluency (5–6 days), endothelial cells were washed twice with Hanks balanced salt solution (HBSS) and stimulated with calcium ionophore A23187 (Sigma, St. Louis, Mo.) at $3\times10^{-6}$M in 1.5 L Eagle's minimum essential medium (MEM) without phenol red (Mediatech, Herdon, Va.). After four hours, the conditioned medium was collected and the cells placed in an additional 2.5 L MEM overnight without further addition of ionophore. The overnight conditioned medium was pooled with the previously collected conditioned medium. For each preparation, approximately four liters of conditioned medium were processed. The stimulated endothelial cell conditioned medium was concentrated to approximately 150 ml using an Amicon concentrator with a 3,000 MW cut off membrane cartridge (Amicon S1Y3, Beverly, Mass.). The concentrated conditioned medium was then adjusted to pH 5.0 by adding MES-Acetate (2-(N-morpholino)ethanesulfonic acetate) to 0.02M, pH 5.0, and precipitated using 12% (w/v) polyethylene glycol (PEG 8000, Sigma) for 30 minutes at room temperature. The PEG-treated concentrated conditioned medium was then centrifuged at 105,000× g for 30 minutes and the supernatant collected. The supernatant was loaded onto a 1×10 cm mono Q anion exchange column (HR10/10, Pharmacia, Piscataway, N.J.) and eluted using a linear gradient of 0.1 to 0.6M NaCl in 0.02M MES-Acetate, pH 5.0, at a flow rate of 2 ml per minute. Two ml fractions were collected and assayed for activity in the TNF inhibition bioassay, described in Example 2. Fractions were assayed at a 1:10 dilution in whole blood for ability to inhibit LPS-induced TNF release.

A gel filtration step was used to further purify the endothelial calmodulin. The active fractions from the mono Q column were pooled and applied to a 1.5×100 cm Sephacryl S-100 HR column previously equilibrated in 0.15M NaCl, 0.02M Tris-HCl, pH 7.5, and 1.0 mM EDTA in TBS. The column was eluted at 8 ml per hour using a peristaltic pump, and 2 ml fractions were collected. The gel filtration column was calibrated using the molecular weight standards of alcohol dehydrogenase (MW 150,000), bovine serum albumin (MW 66,000), carbonic anhydrase (MW 29,000), cytochrome c (MW 12,400), and aprotinin (MW 6,500) (Sigma).

A chromatofocusing step was then utilized to further purify and determine the isoelectric point. A 0.5×20 cm mono P column (HR 5/20, Pharmacia) was equilibrated in 0.025M piperazine-HCl, pH 5.0, and the active fractions from the S-100 HR gel filtration column applied. A linear pH gradient of 5 to 3 was then developed using polybuffer 74 diluted 1:20 and pH adjusted to 2.9 with concentrated HCl (Pharmacia). The flow rate was 1.0 ml/min, and fractions of 0.7 ml were collected and assayed for activity.

At each step, a single peak of activity was identified in the chromatographic fractions. The activity eluted from mono Q at 0.35M NaCl. The apparent molecular weight of the activity was approximately 35 kD by gel filtration, and the isoelectric point was 3.4 by chromatofocusing. After chromatofocusing, the sample was purified to homogeneity as judged by 12% SDS PAGE. Silver staining demonstrated a single negative staining (ghost) band with an apparent molecular weight of approximately 21 kD. Although purified to apparent homogeneity, this preparation was inappropriate for amino acid sequencing due to the presence of polybuffer used to create the pH gradient for the chromatofocusing column. The mono P fraction was therefore further purified using reverse phase high pressure liquid chromatography (HPLC).

A 1×50 mm microbore polymeric reverse phase column (PLRP-S, Michrom Bio Resources) was equilibrated in 0.1% (v/v) trifluoroacetic acid, 2% (v/v) acetonitrile in water. The active fractions from the mono P column were applied and the column washed. The column was then eluted using a linear gradient of acetonitrile to 50% over 15 min using a flow rate of 0.06 ml/min and collecting 0.05 ml fractions.

Amino acid analysis was performed after acid hydrolysis on an automated Beckman system Gold HPLC amino acid analyzer.

An independent lab also performed amino acid analysis (Harvard Micro Chem, Cambridge, Mass.). Table 1 shows similar results obtained from both labs which compares well to the known amino acid composition of calmodulin.

To obtain internal sequence information, a trypsin digest was accomplished and the resulting fragments separated by HPLC using a C18 column. The eluted fragments were analyzed in-line with electro-spray mass spectrometry as well as absorbance at 220 nm. The sequence was obtained from three fragments. This sequence information was entered into the GCG program and a search of known sequences in the swiss-prot database performed. The amino acid sequence of tryptic fragments identified the endothelial factor as calmodulin with 100% identity through 40 amino acids. The three sequences obtained corresponded to amino acids #76 to 126 of authentic calmodulin. The size of three fragments by mass spectroscopy corresponds to predicted tryptic fragments of calmodulin as shown in Table 2. A fourth fragment yielded no sequence and corresponds in molecular mass to the N-terminal tryptic fragment of calmodulin which is known to be blocked because of acetylation.

TABLE 1

AMINO ACID ANALYSIS OF ENDOTHELIAL CELL CALMODULIN

| AA | Predicted # | Measured | Independent Lab |
|----|-------------|----------|-----------------|
| ASX | 23<br>17 ASP + 6 ASN | 24 | 23 |
| GLX | 27<br>21 GLU + 6 GLN | 27 | 27 |
| SER | 4 | 4 | 3 |
| GLY | 11 | 11 | 11 |
| HIS | 1 | 1 | 1 |
| ARG | 6 | 6 | 9 |
| THR | 12 | 12 | 12 |
| ALA | 11 | 11 | 11 |
| PRO | 2 | 2 | 3 |
| TYR | 2 | 2 | 2 |
| VAL | 7 | 7 | 7 |
| MET | 9 | 7 | 9 |
| ILE | 8 | 8 | 7 |
| LEU | 9 | 10 | 9 |
| PHE | 8 | 9 | 8 |
| LYS | 8 | 7 | 7 |
| CYS | 0 | — | — |
| TRP | 0 | — | — |

To exclude the possibility that the endothelial factor was a modified form of calmodulin, both authentic calmodulin from hog brain and the purified endothelial factor were subjected to ion-spray mass spectrometry for the determination of molecular weight (MW). Both species of calmodulin had a similar spectral pattern. The MW for authentic hog brain calmodulin was 16,788.65, and the MW for endothelial calmodulin was 16,785.77. The value obtained for the endothelial factor (16,785.77±1.75 daltons) agrees well with the predicted molecular weight of calmodulin of 16,790 (16,706 as calculated by the GCG package for the amino acid sequence, plus 84 for the known trimethylation of lysine 115 and acetylation of the N-terminus) and with the value obtained for hog brain calmodulin (16,788.65±1.11 daltons).

TABLE 2

TRYPTIC FRAGMENTS OF ENDOTHELIAL CELL CALMODULIN

| Peak | AA # | Measured MW | Predicted MW |
|------|------|-------------|--------------|
| 2 | 91–106 | 1754.9 | 1754.9 |
| 3 | 75–86 | 1984.3 | 1984.9 |
| 4 | 107–126 | 2401.1 | 2401.1 |
| 7 | 1–74 | 1562.9 | 1562.74 |

In the following examples, TNF release and the inhibition by calmodulin varied substantially from subject to subject, often several-fold within a given experiment. This indicates that the ability of calmodulin to inhibit TNF production varies widely between subjects, setting the framework to use such assays to predict calmodulin responders in a diagnostic manner. To normalize data in the experiments below, we commonly expressed the effect of calmodulin as a percent inhibition of the control response for each subject; the mean of these values was then calculated, and if the 95% confidence interval on this mean did not include zero, the inhibition was regarded as statistically significant. Experiments with larger numbers of subjects and with multiple treatment groups run in parallel were analyzed by a two-way analysis of variance, with treatment condition as fixed effect and subject as random effect. Subsequent intergroup comparisons were made by t-tests using the pooled mean square error from the ANOVA and with the Bonferroni correction for multiple comparisons, or by Scheffé's test (Kleinbaum et al., *Applied Regression Analysis and Other Multivariable Methods*, Duxbury Press, Boston 1978). Unless otherwise stated, data are presented as mean±s.e.m.

EXAMPLE 2

Measurement of TNF Activity

Immunoreactive TNF was measured using a sandwich ELISA sensitive to ≈0.1 ng/ml TNF. 96-well Immulon IV microtiter plates (Dynatech, Chantilly, Va.) were coated overnight at 4° C. with a monoclonal anti-TNF antibody, TNF 1286 or TNF 1311 (5 µg/ml in TBS, 50 µl per well).

For antibody production, female Balb/c mice at 9 weeks of age were immunized intraperitoneally with 100 µg of recombinant human TNF-α (Genentech, South San Francisco, Calif.) in 200 µl Freund's complete adjuvant (Difco, Detroit, Mich.). Mice were boosted with an additional 100 µg TNF four weeks after primary immunization and hybridoma cell fusion was performed four days later. Spleens were aseptically removed, minced, washed, and mixed with the P3X63Ag8-653 fusion partner (ATCC, Rockville, Md.) in a ratio of five to one. The cells were fused with polyethylene glycol (PEG 1500, Boehringer Mannheim, Indianapolis, Ind.) and plated into six 96-well plates (Costar, Cambridge, Mass.) containing resident peritoneal exudate cells from Balb/c mice as a feeder layer. Resulting hybridomas were cultured in HAT medium for 10 days, HT medium for 2 weeks, and then maintained in RPMI 1640 (Mediatech, Herndon, Va.) with 10% (v/v) bovine calf serum (Hyclone, Logan, Utah). Hybridomas were screened for their ability to react with TNF in a plate binding assay. 96-well plastic microtiter plates (Costar) were coated overnight with 50 µl per well of TNF, 1 µg/ml, in TBS. Plates were blocked for one hour with 1% bovine serum albumin (BSA, Sigma, St. Louis, Mo.) in TBS, washed, and 50 µl samples of hybridoma supernatants applied for one hour.

Plates were then washed and polyclonal IgG-specific goat anti-mouse antibody conjugated to horseradish peroxidase (0.1 μg/ml in TBS/0.1% BSA; Kirkegaard & Perry Laboratories, Gaithersburg, Md.) applied for one hour. Plates were washed a final three times, ABTS substrate (Kirkegaard & Perry) applied, and reactivity scored visually.

Polyclonal antibody to TNF was produced in a goat by immunization with TNF, 1 mg in 2 ml complete Freund's adjuvant (Difco) using a combination of subcutaneous, intradermal, and deep intramuscular routes. Six weeks later the goat was boosted with an additional 1 mg TNF in TBS and serum collected at weekly intervals thereafter. This antiserum (#188) titered to 1:500,000 using a plate binding assay as described above.

Antibodies (total IgG fraction from goat serum and monoclonal antibodies from mouse ascites) were purified using a protein G affinity column (Pharmacia, Piscataway, N.J.) according to the manufacturer's directions. The polyclonal anti-TNF #188 antibody was biotinylated using NHS-LC-biotin (Pierce, Rockford, Ill.) according to the manufacturer's recommendations.

The next morning the ELISA plates were washed three times with TBS with 0.1% (v/v) Tween 20 (Sigma) and blocked for one hour with 1% BSA in TBS. Plates were then washed three times. Plasma samples were diluted 1:5 in 0.1% BSA in TBS, and 50 μl/well pipetted onto the plates and allowed to incubate at 37° C. for one hour. TNF standards were made up by addition of known amounts of recombinant human TNF-α (Upstate Biologicals Inc., Lake Placid, N.Y.) to pooled heparinized normal plasma diluted 1:5 in TBS/BSA. All samples and standards were assayed in duplicate. Plates were washed three times and biotinylated goat anti-TNF antibody or biotinylated monoclonal TNF 1289 (2 μg/ml in 0.1% BSA in TBS, 50 μl/well) was applied and incubated at 37° C. for one hour. Plates were washed three times and streptavidin-alkaline phosphatase (Gibco BRL, Grand Island, N.Y.) (0.025 μg/ml in 0.1% BSA in TBS, 50 μl/well) was applied and incubated at 37° C. for one hour. Following a final four washes, an amplified substrate (Gibco BRL) was applied according to the manufacturer's directions. Plates were read at 492 nM on a microtiter plate reader (Molecular Devices, Palo Alto, Calif.) and values obtained by comparing unknowns to a standard curve using a four-parameter fit. The useful range of this assay was 1–50 ng/ml.

EXAMPLE 3

Measurement of Neutrophil Elastase Activity

Figure 2:
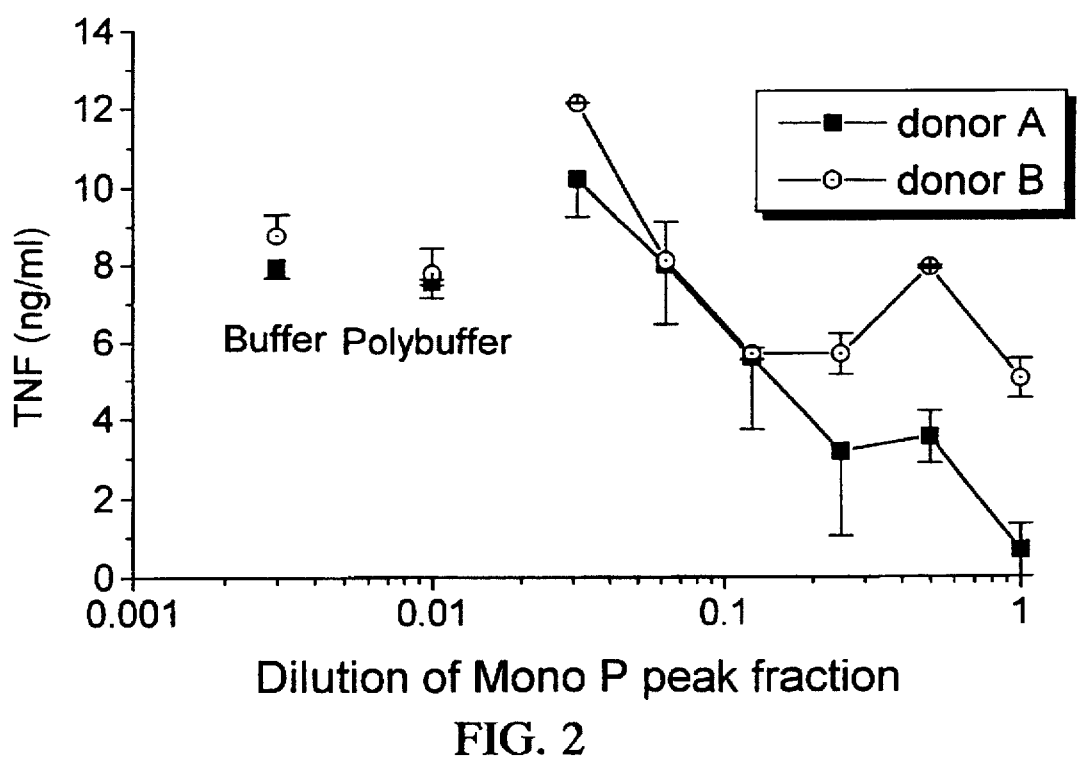
FIG. 2 is a graph depicting the augmentation of elastase release in whole blood by purified endothelial cell calmodulin.

An assay similar to that described in Example 2 was developed for neutrophil elastase in the same plasma samples (measured as the complex between elastase, and α-1-antitrypsin) using a murine monoclonal antibody (HEL 1076) to elastase as capture and biotinylated murine monoclonal antibody (HAT 1099) as detector. The useful range of this assay was 0.05 to 5 nM complex. These antibodies were obtained by immunizing mice with human neutrophil elastase, human α-1-antitrypsin (Athens Research and Technology, Athens, Ga.) and a complex of both using the method detailed in Example 2. Antibodies were screened for their ability to react with native and complexed antigen. Antibodies were purified from ascites using protein G (Pharmacia, Piscataway, N.J.) affinity chromatography and biotinylated using NHS-LC-biotin (Pierce). In addition to the inhibition of TNF release, calmodulin also augmented elastase release similar to that observed with the endothelial cell monolayer (FIG. 1, authentic calmodulin; FIG. 2, purified endothelial cell calmodulin).

EXAMPLE 4

Verification of the Identity of Calmodulin

Chromatographic fractions of endothelial conditioned media were assayed for the ability to inhibit LPS-induced TNF release by the addition in a ⅒th volume to the whole blood just prior to stimulation with LPS. After purification to apparent homogeneity, the endothelial factor was digested with trypsin and the tryptic fragments separated for amino acid sequencing. Amino acid sequences from three fragments identified the endothelial factor as calmodulin with 100% identity through 40 amino acids. By mass spectrometry, there was no difference between endothelial and hog brain calmodulin.

Figure 3A:
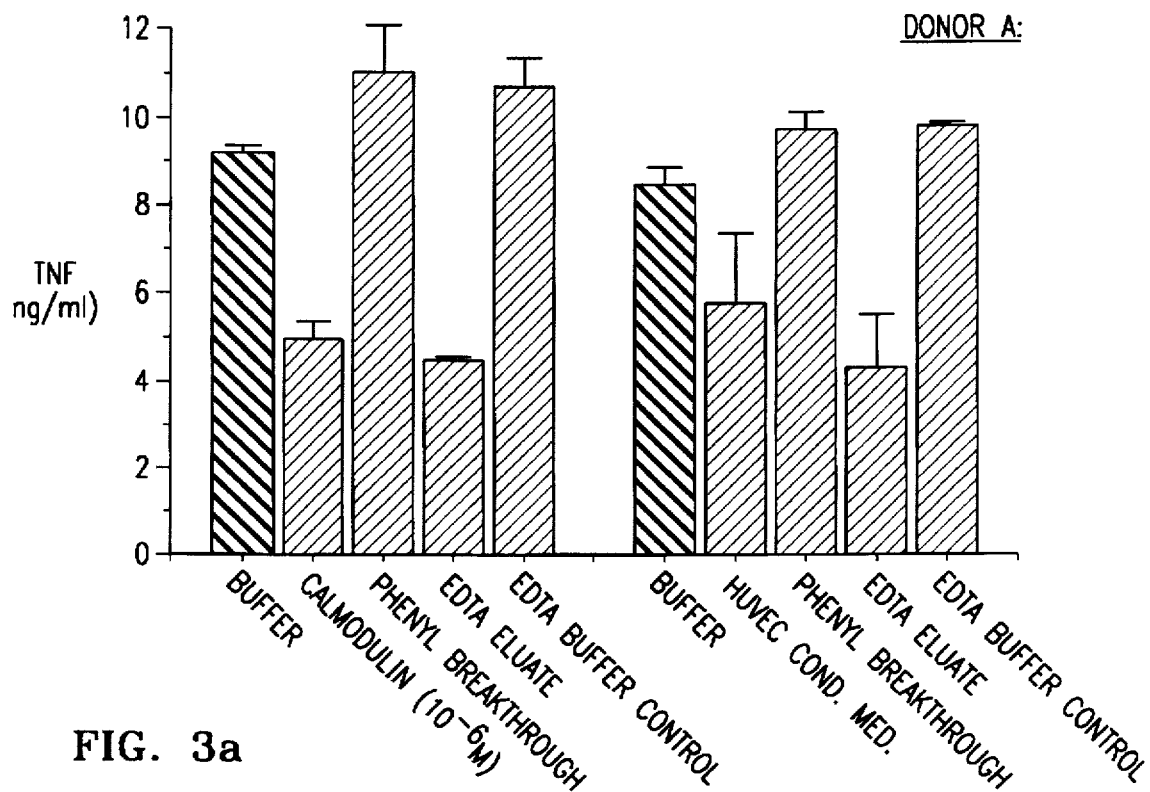
FIGS. 3a and 3b are graphs depicting the TNF inhibiting activity of endothelial cell releasate following binding to a phenyl sepharose column in the presence of calcium and eluting with EDTA (ethylenediaminetetraacetic acid) for Donor A and Donor B, respectively.
Figure 3B:
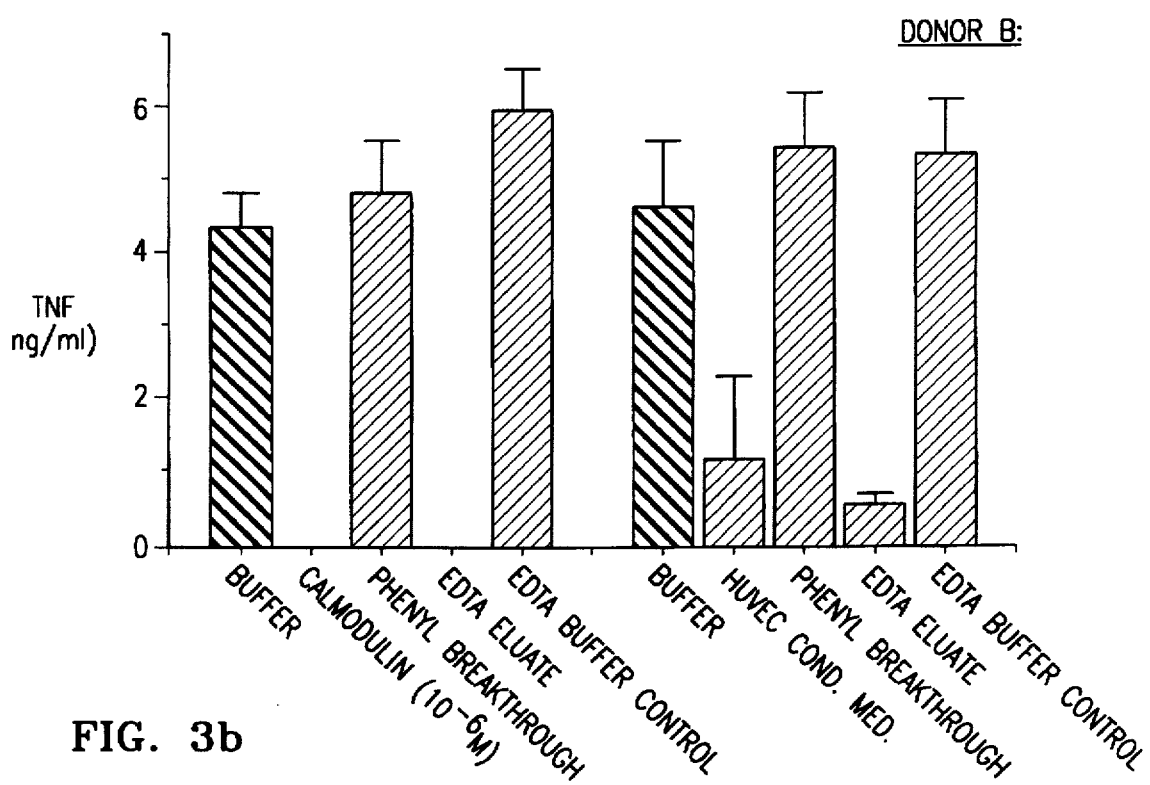

Calmodulin in the calcium conformation possesses a hydrophobic patch and binds to immobilized phenyl and can be eluted with EDTA. An endothelial sample to be evaluated for calcium-dependent binding to phenyl groups was loaded onto a 0.5×5.0 cm phenyl-superose column (HR 5/5, Pharmacia, Piscataway, N.J.) and washed sequentially with 0.1 mM $CaCl_2$, 0.5M NaCl, 0.02M Tris-HCl, pH 7.5; then washed with 0.1 mM $CaCl_2$, 0.02M Tris-HCl, pH 7.5; and finally eluted with 1 mM EDTA, 0.02M Tris-HCl, pH 7.5, at a flow rate of 2 ml/min, collecting 0.7 ml fractions. FIG. 3a and FIG. 3b demonstrate the selective removal of TNF inhibiting activity by phenyl-superose and elution of TNF inhibiting activity from this column by EDTA.

EXAMPLE 5

Concentration of Calmodulin

Calmodulin concentration in the chromatofocusing fraction described in Example 1 was assayed by several methods and the results are summarized in Table 3.

The amount of calmodulin present in the chromatographic fraction was estimated by comparing the activity of authentic hog brain calmodulin with dilutions of the active chromatographic fraction using the TNF release assay given in Example 2. This gave an estimated 138 μg/ml. The calmodulin concentration was determined by a functional phosphodiesterase assay as described by Wallace, et al., "Assay of calmodulin by calcium dependent phosphodiesterase," Methods of Enzymology, 102:39–47 (1983). Samples to be assayed or standards were combined with bovine brain phosphodiesterase (Sigma, St. Louis, Mo.) and $^3$H-cyclic AMP. After incubation at 37° C., the AMP generated was converted to adenosine with 5' nucleotidase present in Crotolus atrox venom, and the $^3$H-adenosine quantitated. The calmodulin concentration was estimated by this method at 128 μg/ml. An estimate by radioimmunoassay (RIA) was 530 μg/ml, and the total protein concentration by the BCA protein assay was 332 μg/ml. These differences are likely within the error of the assays. The antibodies provided in the RIA demonstrate markedly enhanced reactivity with calmodulin that has been slightly denatured, as with heat. It is likely that some of the calmodulin detected by RIA and protein assay may have been subtly denatured by one of the purification steps, such as exposure to low pH during chromatofocusing leading to overestimation by this procedure. Calmodulin retains calcium during electrophoresis and demonstrates a shift in mobility compared to electrophoresis in the presence of EDTA.

TABLE 3

CALMODULIN IN CHROMATOGRAPHIC FRACTION

| Assay | Calmodulin Conc. |
| --- | --- |
| Functional | 138 µg/ml |
| Phosphodiesterase | 128 µg/ml |
| RIA | 530 µg/ml |
| Protein (BCA) | 332 µg/ml |

EXAMPLE 6

Measurement of TNF Activity with Other Calmodulins

Figure 4:
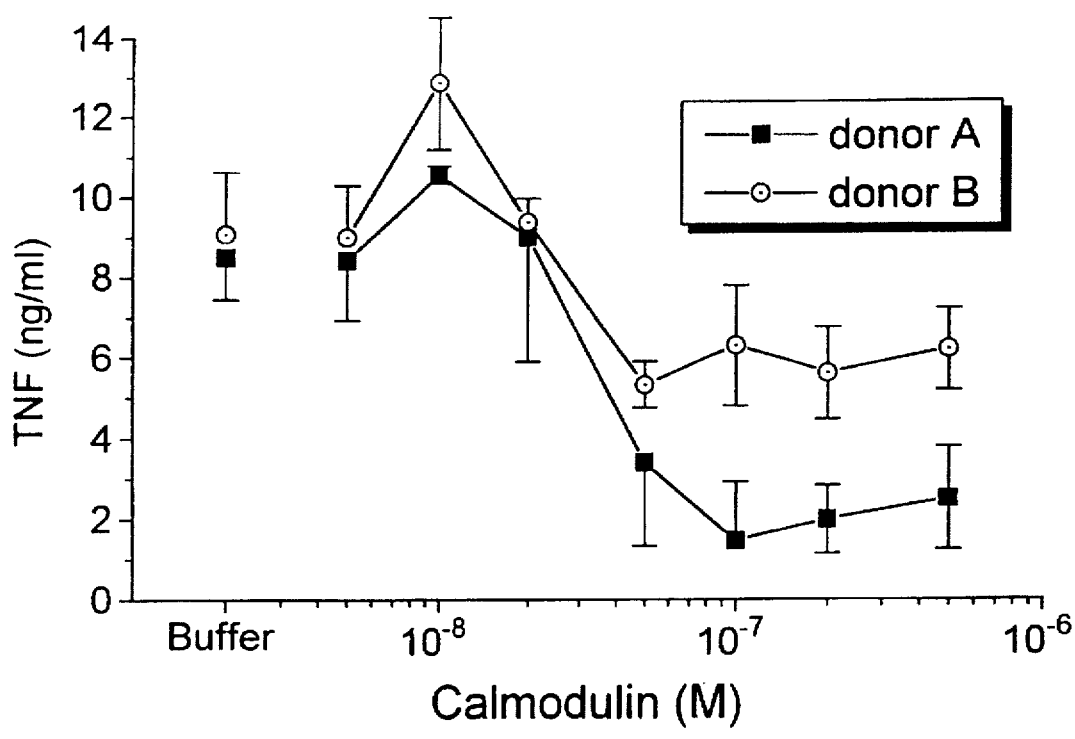
FIG. 4 is a graph depicting the inhibition of TNF release in whole blood by authentic (hog brain) calmodulin.
Figure 5:
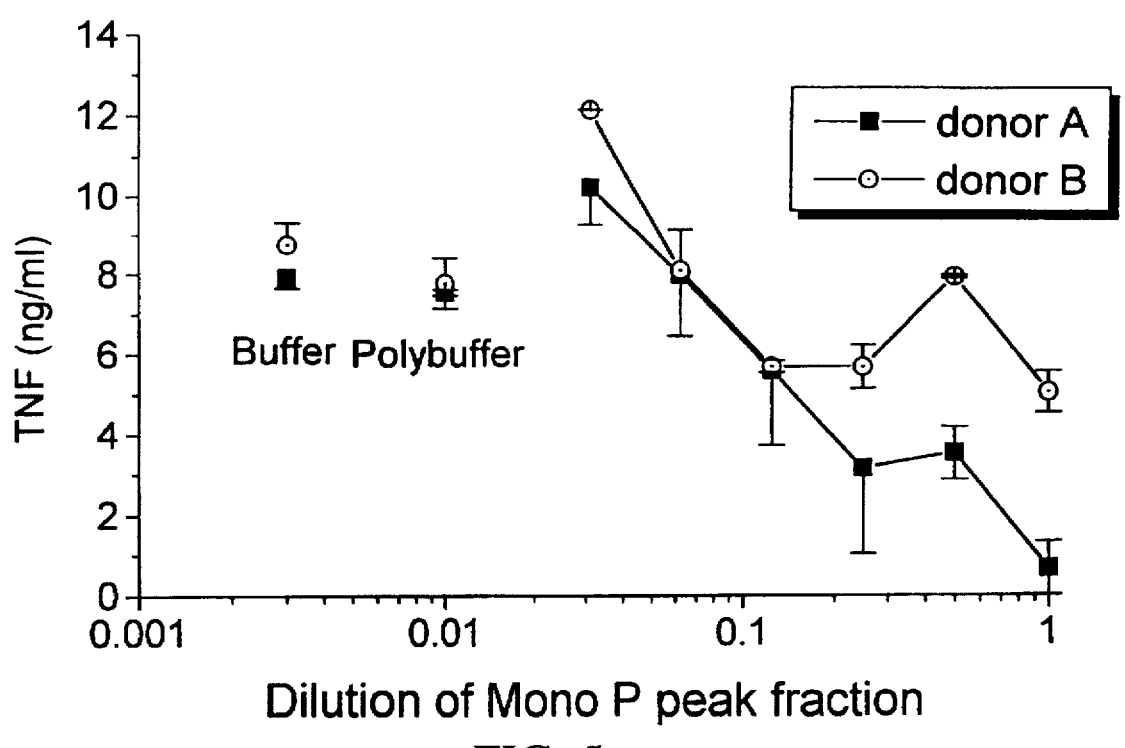
FIG. 5 is a graph depicting the inhibition of TNF release in whole blood by purified endothelial cell calmodulin.

Authentic calmodulin was obtained from human RBC, hog brain, and bovine testes. Each of these calmodulins demonstrated inhibition of TNF production in the whole blood assay system. Maximum inhibition of TNF production (50–60%) was observed at $1 \times 10^{-7}$M and half maximal inhibition at $3 \times 10^{-8}$M calmodulin. Examples of TNF-inhibition are given for authentic hog brain calmodulin (FIG. 4) and calmodulin derived from endothelial cells (FIG. 5).

EXAMPLE 7

Additive Effect of Calmodulin and HUVEC

To determine whether the effect of the HUVEC monolayer was indeed due to calmodulin, experiments were performed to determine whether the effects of an endothelial cell monolayer and calmodulin were additive. Calmodulin or buffer control was added to blood incubated over aspirin-treated endothelial cell monolayers or control wells without endothelium and stimulated with LPS. As a positive control, the additivity of the effect of submaximally inhibitory concentrations of prostaglandin $E_2$ ($PGE_2$) with the effect of calmodulin or HUVEC monolayers was also evaluated.

Figure 6:
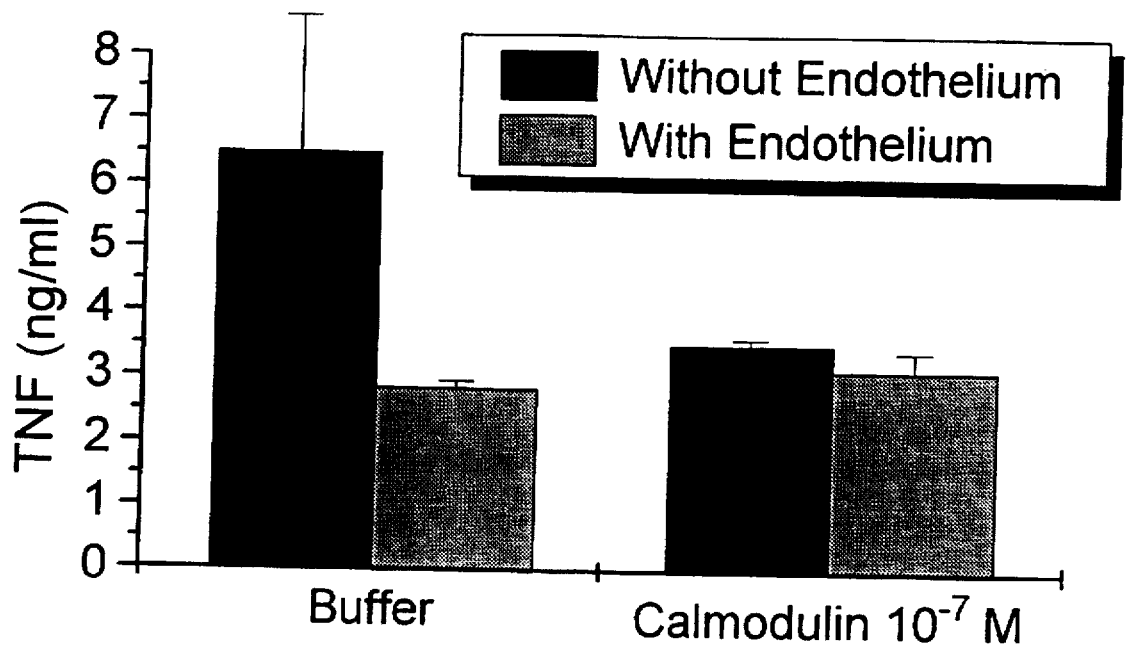
FIG. 6 is a graph depicting the additive effect of exogenous calmodulin and the endothelial cell monolayer for Donor A.
Figure 7:
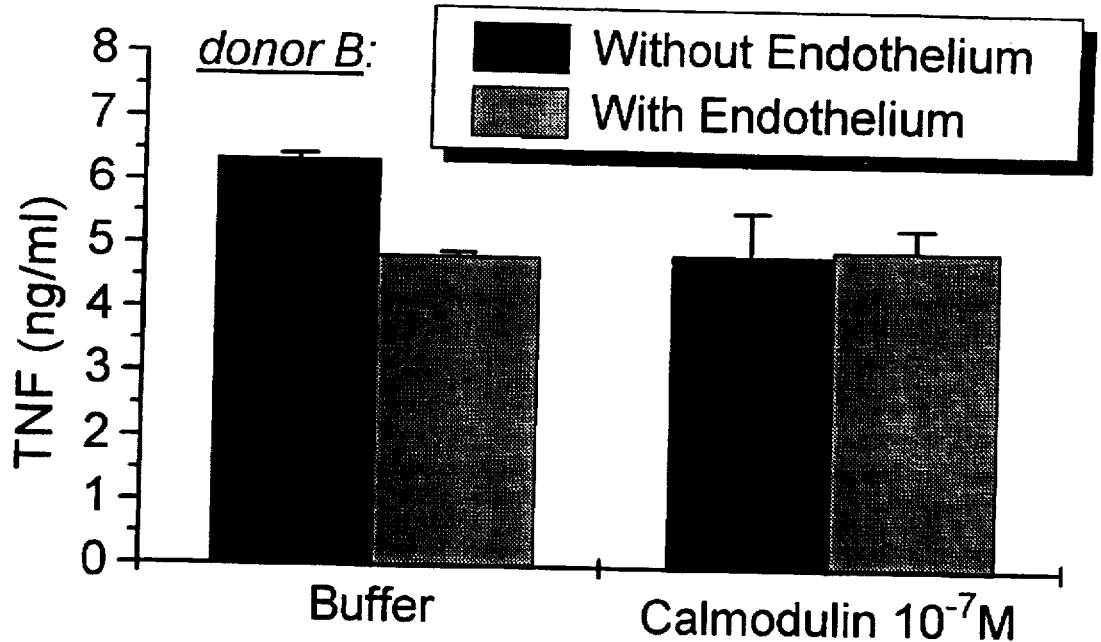
FIG. 7 is a graph depicting the additive effect of exogenous calmodulin and the endothelial cell monolayer for Donor B.
Figure 8:
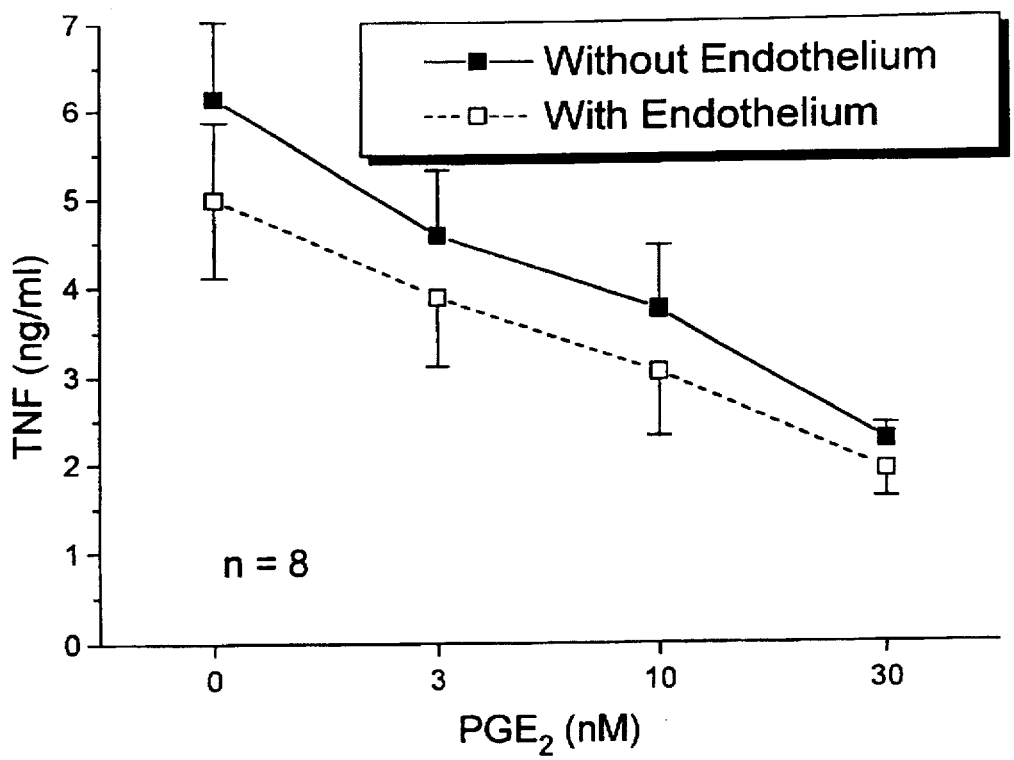
FIG. 8 is a graph depicting the additive effect of endothelial cell monolayer and $PGE_2$.
Figure 9:
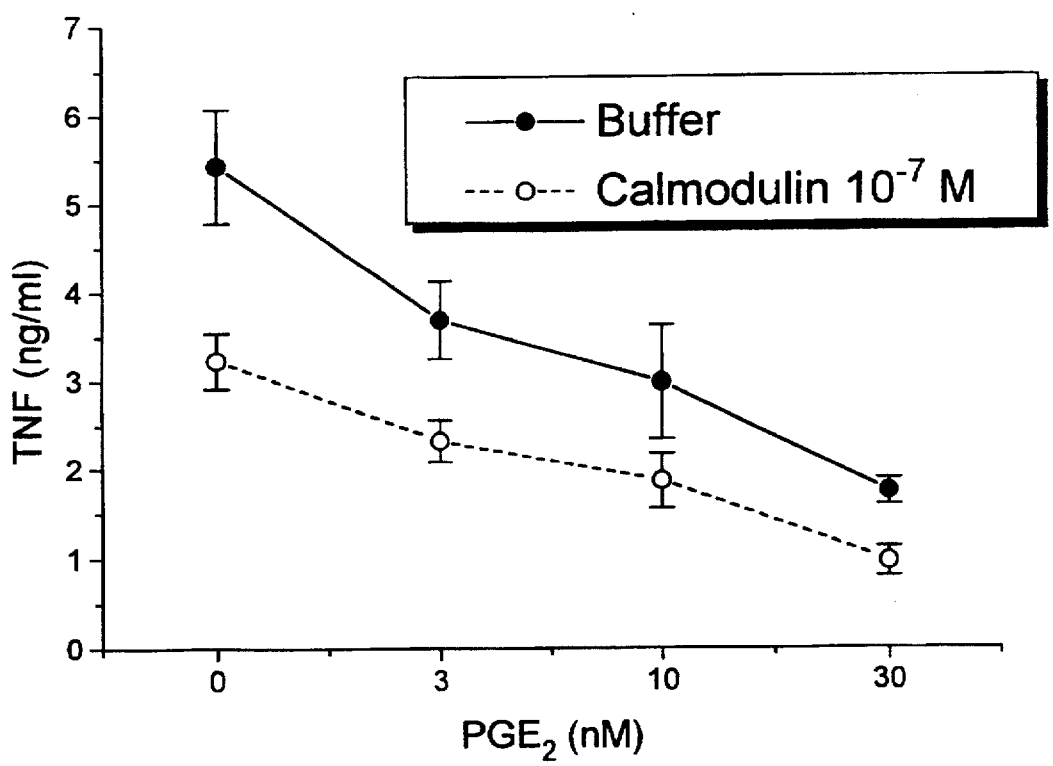
FIG. 9 is a graph depicting the additive effect of exogenous calmodulin and $PGE_2$.

Having noted that the maximal inhibitory effects of the endothelium and of authentic calmodulin were similar (on the order of 50%), we reasoned that if the activity of the endothelial monolayer were due to calmodulin, then the addition of a maximally active concentration of exogenous calmodulin ($10^{-7}$M) to blood incubated over endothelium would result in no further inhibition of TNF release than occurred with either endothelium or calmodulin alone. As shown in FIG. 6 and FIG. 7, this was the case. In contrast, if the endothelial TNF-inhibiting effect were due to an unrelated mediator, then the effects should be additive. This indeed was the case with the known inhibitor of TNF release, $PGE_2$. In doses causing roughly 50% inhibition of TNF release, $PGE_2$ augmented the effects both of the endothelial monolayer and of authentic calmodulin (FIG. 8 and FIG. 9).

EXAMPLE 8

TNF Message

Figure 10:
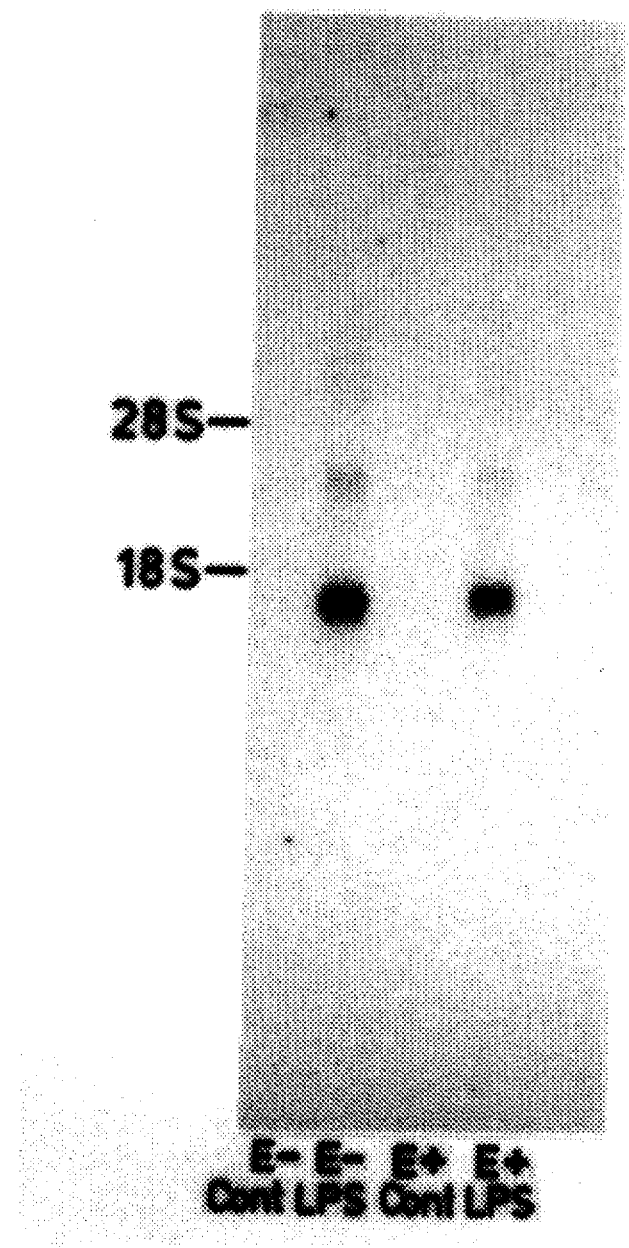
FIG. 10 is a representation of Northern blots of TNF mRNA inhibited by endothelial cells.

TNF message was detected in the total cellular RNA from mononuclear cells in whole blood treated as described above. After a one hour incubation period with LPS±calmodulin or HUVEC monolayer, the blood was collected and carefully layered over Histopaque 1077 (Sigma, St. Louis, Mo.) at 400× g for 30 minutes. The mononuclear cell fraction was collected and washed twice with ice-cold PBS. The total cellular RNA was then isolated using the acid, guanidinium thiocyanate-phenol-chloroform extraction method of Chomczynski, et al., *Analytical Biochemistry* 162:156–159 (1987). Resulting RNA was quantitated by absorption at 260 nm and five micrograms of total mononuclear cell RNA was electrophoresed in 1% agarose, 1.8% (0.61M) formaldehyde gels and transferred to Hybond N+ membranes (Amersham, Arlington Heights, Ill.). RNA was fixed to the membranes using 50 mM NaOH and washed with 20× SSC (an aqueous buffer containing 3M NaCl and 0.34M sodium citrate adjusted to pH 7 with NaOH). The membranes were prehybridized in 5× Denhardt's reagent, 6× SSC (0.9M NaCl and 0.1M sodium citrate adjusted to pH 7 with NaOH), 0.5% SDS (sodium dodecyl sulfate), 50% formamide, and 100 µg/ml salmon sperm DNA. TNF cDNA probe was labeled with $^{32}$P using the random-primer technique (Amersham) according to the manufacturer's directions and added to the membranes for at least 12 hours in the same hybridization buffer. After hybridization, filters were washed and then exposed to X-OMAT HR film (Kodak, Rochester, N.Y.) at −70° C. Message size was determined by staining with ethidium bromide (0.5 mg/ml) and comparing to 28S and 18S ribosomal RNA. Quantitation of TNF message was performed using AMBIS radiodensitometry system. As shown in the TNF mRNA Northern blots in FIG. 10, there was partial inhibition of TNF mRNA in response to HUVEC or calmodulin.

EXAMPLE 9

Effects of Endothelial Cell Monolayer on TNF and Elastase

Figure 11:
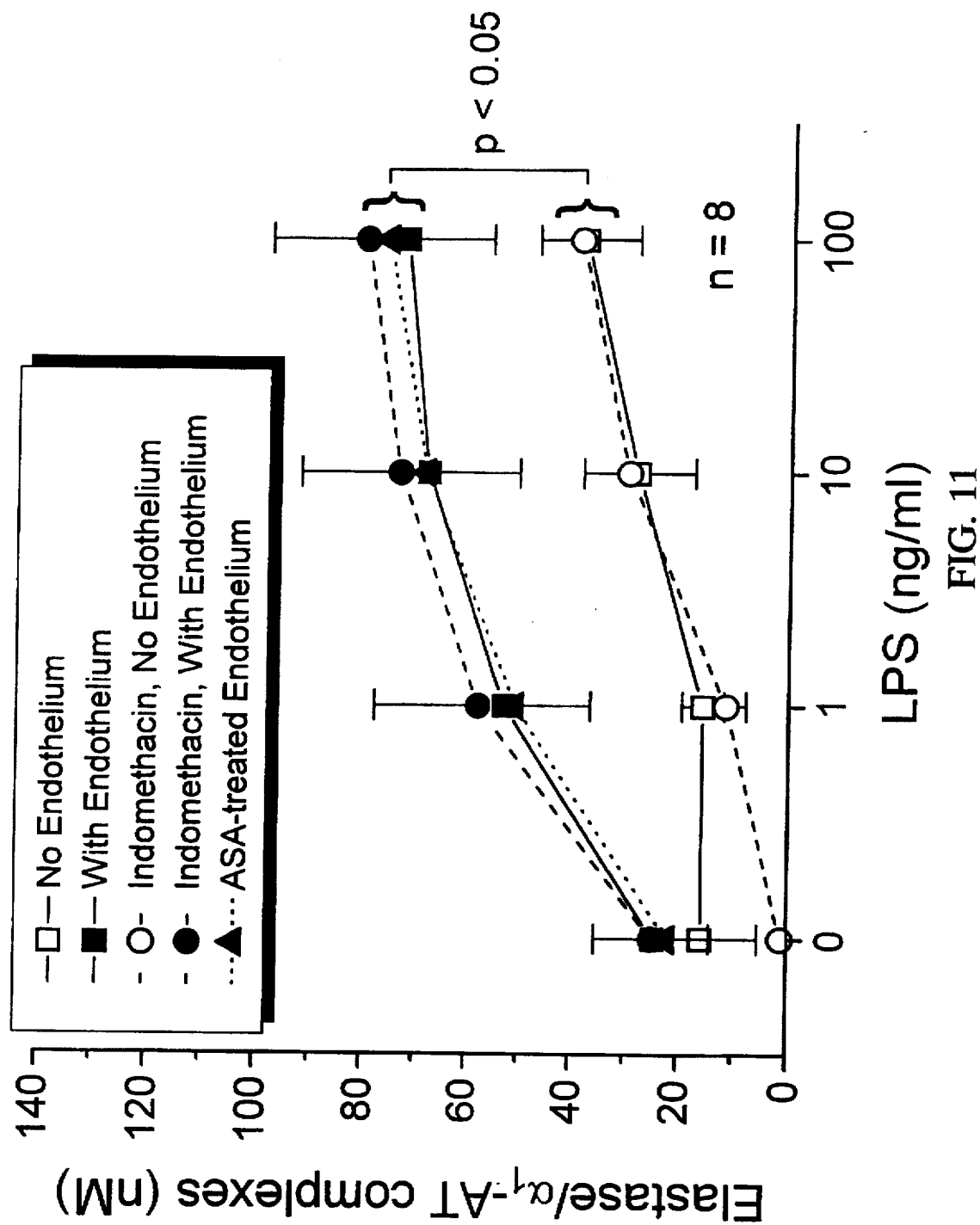
FIG. 11 is a graph depicting augmentation of elastase release in whole blood by HUVEC monolayers in the presence of indomethacin or aspirin.

Human umbilical vein endothelial cell monolayers demonstrated the ability to inhibit endotoxin-induced TNF release in whole blood by approximately 50–60% as previously described in Example 6. In addition, elastase release in whole blood measured as the complex of elastase with α-1 protease inhibitor (α-1 antitrypsin) was augmented by the presence of an endothelial cell monolayer as shown in FIG. 11 (n=8). This observed augmentation of elastase release was present at all concentrations of endotoxin and at all time points observed from 15 minutes to 12 hours. Augmentation of elastase release was not changed by treatment with aspirin or indomethacin known to inhibit prostaglandin production.

EXAMPLE 10

Effect of Endothelial Cells on LPS-induced TNF Release in Whole Blood

Blood from healthy volunteers was drawn from the antecubital vein into a heparinized syringe (10 U/ml final; UpJohn, Kalamazoo, Mich.). 24-well culture plates (Costar, Cambridge, Mass.) were coated with 2% (w/v) gelatin (Sigma) and washed three times with Hanks balanced salt solution (HBSS) (Gibco BRL, Gaithersburg, Md.). Only the center eight wells were used to minimize evaporation. Then, 200 µl of blood was pipetted into each well. For comparative experiments involving endothelial cell monolayers, endothelial cells were seeded onto gelatin-coated wells at 3–5× $10^5$ cells per well 48 hours prior to experimentation. These wells were washed three times with HBSS and heparinized whole blood added as above. In most cases, the same plate would contain wells with and without endothelium for comparison purposes.

Test reagents suspended in HBSS (8 to 10 µl) were added to the wells immediately after the blood. Plates were incubated at 37° C. in room air/5% $CO_2$ on an orbital shaker at 150 rpm; incubations were four hours unless otherwise noted. The blood then was transferred to microcentrifuge tubes and centrifuged at 500× g for 10 minutes. The resulting platelet-poor plasma was collected and assayed for TNF immediately, as per Example 2 or stored frozen at −70° C. until use.

In most experiments, LPS (from *E. coli* strain 055:B5, Difco) was used to stimulate TNF release. Other agonists used were zymosan (Sigma, St. Louis, Mo.), muramyl dipeptide (Sigma), recombinant human interferon-γ (Mallinckrodt, Paris, Ky.), and recombinant human interleukin-1β (Collaborative Research, Bedford, Mass.). In some experiments, prostaglandin $E_2$ ($PGE_2$) and the stable prostacyclin analogue, carbacyclin (both from Cayman Chemical, Ann Arbor, Mich.) were added just before the LPS. These were dissolved as a $2.84 \times 10^{-3}$M stock solution in DMSO and diluted in HBSS; buffer controls with the same concentrations of DMSO were assayed in parallel.

Incubation of whole blood with LPS for four hours evoked a dose-dependent release of TNF. In control wells not treated with LPS, TNF levels were usually below the limit of detection by our ELISA (approx. 1 ng/ml). In preliminary observations, a biphasic dose-response relationship was seen, as has been described by others Aderka, et al., *J. Immunol.* 143:3517–3523 (1989): an initial response at concentrations of 1 to 100 ng/ml, then a plateau, followed by a second increase with concentrations over 1 μg/ml. On the assumption that the lower concentration range may be of greater physiological relevance, subsequent experiments were performed with LPS concentrations between 1 and 100 ng/ml.

Figure 12:
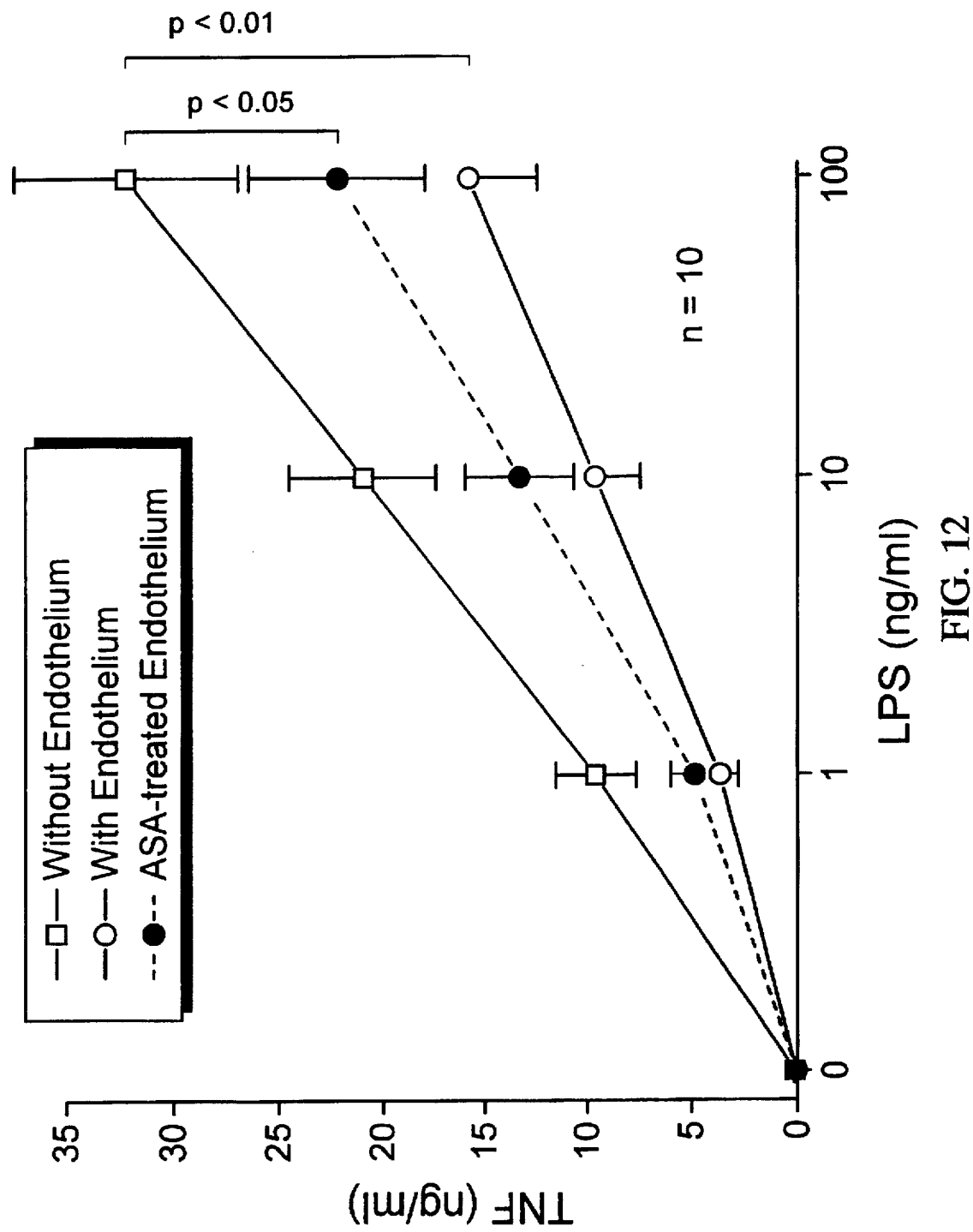
FIG. 12 is a graph depicting inhibition of lipopolysaccharide (LPS)-induced TNF release in whole blood by endothelium.

When blood treated with LPS was incubated over an endothelial monolayer for four hours, TNF release was decreased on average by about 50% at all concentrations of LPS (FIG. 12; n=10). It should be noted, however, that in addition to the variability in TNF release between donors, there was considerable variability in the extent of inhibition, both between donors and between endothelial cell preparations. In the data for 100 ng/ml LPS from FIG. 12, for example, with ten subjects each assayed on endothelial cells from three cords, the coefficient of variation for TNF values was 69%. Even when data were expressed as a percent of that subject's own control response, the coefficient of variation was 61% (the average inhibition 49% with a standard deviation of 30%, a median of 56%, a minimum of −38% and a maximum of 88%).

Figure 13:
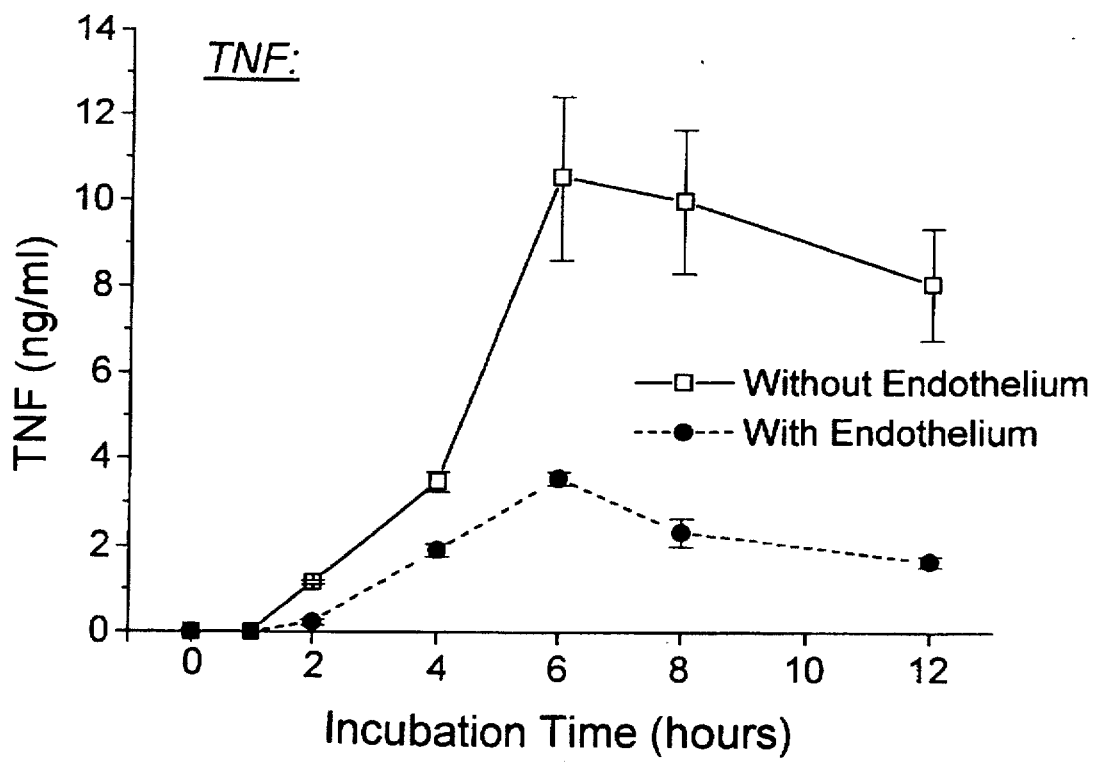
FIG. 13 is a graph depicting the effect of endothelium on the time course of TNF release in whole blood after the addition of LPS.
Figure 14:
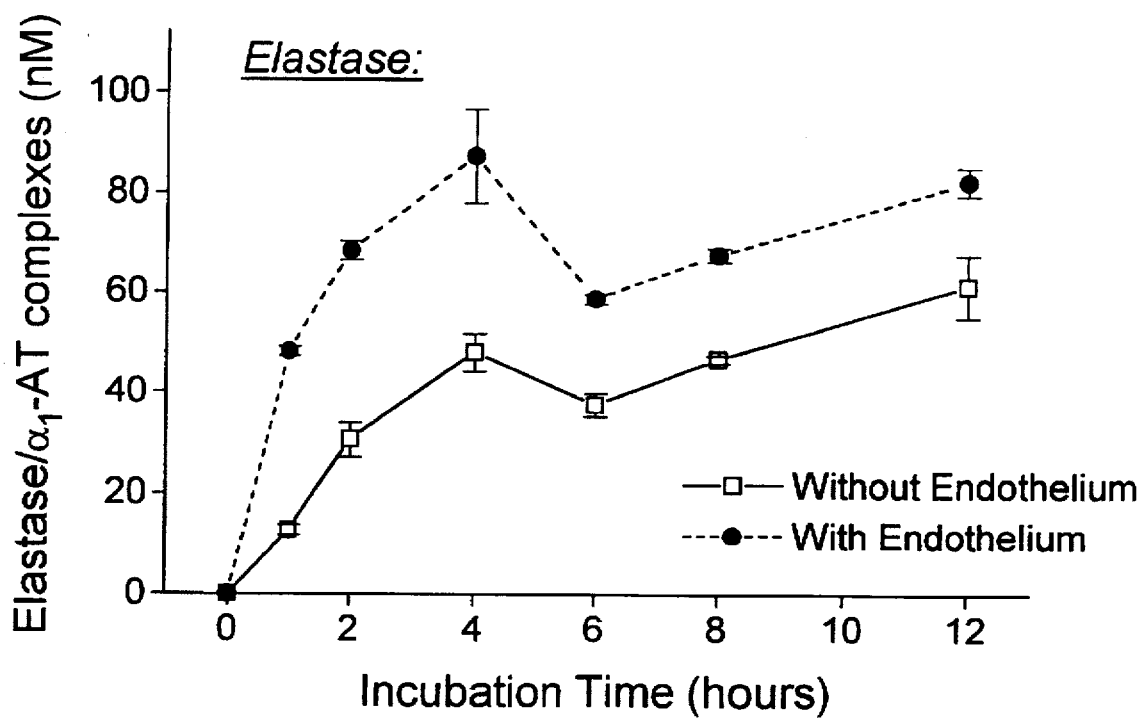
FIG. 14 is a graph depicting the effect of endothelium on the time course of elastase release in whole blood after the addition of LPS.
Figures 15A, 15B, 15C, 15D:
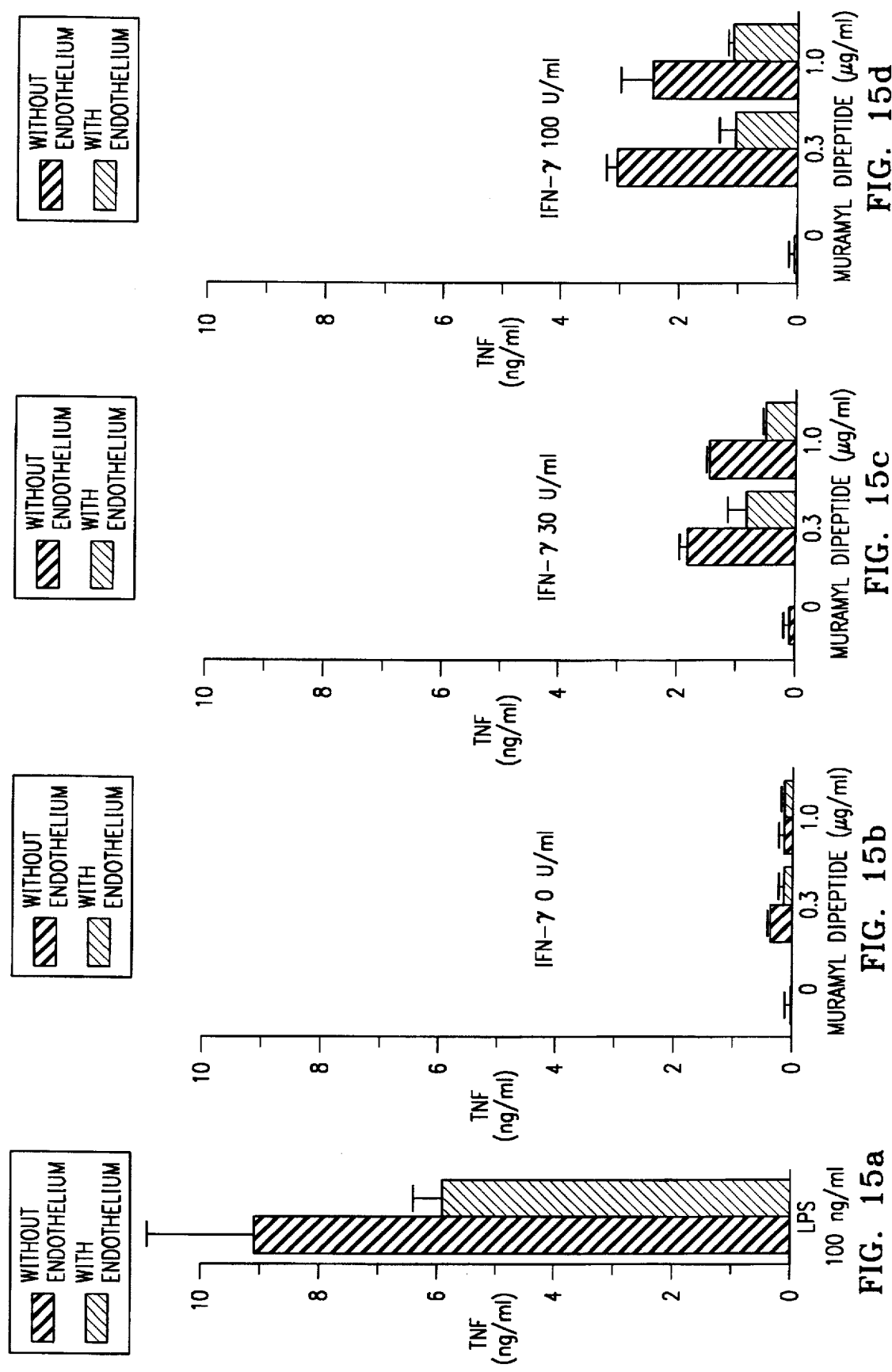
FIG. 15a, FIG. 15b, FIG. 15c, and FIG. 15d are graphs depicting the effect of endothelium on TNF release in whole blood in response to various concentrations of muramyl dipeptide and/or interferon-γ.

TNF became detectable within 2 hours after addition of LPS, peaked at 6 hours, and declined slightly to 12 hours. In the presence of an endothelial monolayer, less TNF was produced at each time point studied (FIG. 13). There was no change in the temporal pattern of release, indicating that the inhibition of TNF release observed at four hours does not reflect a delay in the release of TNF. Comparatively, an increase in elastase release was observed in the presence of the endothelial monolayer (FIG. 14).

The decrease in measured TNF in the presence of endothelium might be attributable to an increased clearance of TNF rather than a decrease in the amount of TNF released. To rule out this possibility, blood samples (without LPS) were spiked with exogenous TNF. The recovery of TNF (5, 20, 40 or 80 ng/ml) after 4 hours was not significantly reduced (6.7±4.0% less) when the blood was incubated in the presence of an endothelial monolayer (n=6).

Endothelial cells may bind LPS (Hampton, et al., *Nature* 352:342–344 (1991)), and the possibility exists that the decreased TNF release observed in the presence of endothelial cells may be due to clearance of the LPS. As an indirect test of this possibility, other stimuli for TNF release were examined. Muramyl dipeptide and interferon-γ (0.3 to 1 μg/ml and 30 to 100 units/ml, respectively) were weak agonists, alone, but synergistically evoked TNF release in whole blood. In the presence of indomethacin ($10^{-6}$M) to exclude any effect of prostaglandins, the responses to these agonists were inhibited by endothelium to a similar degree as the response to LPS (FIGS. 15a, 15b, 15c, and 15d).

Figure 16:
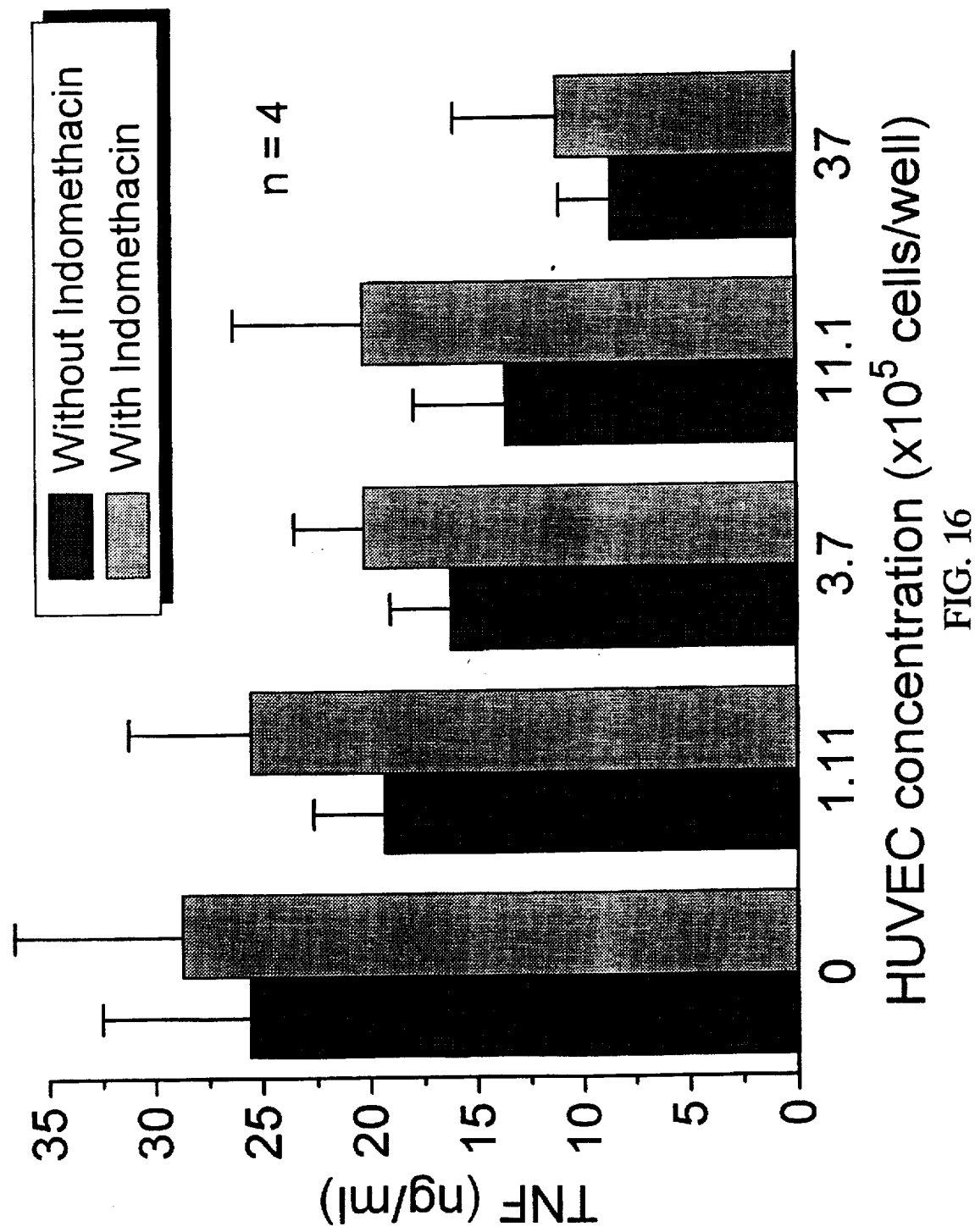
FIG. 16 is a graph depicting inhibition of LPS-induced TNF release in whole blood by endothelium in the presence or absence of indomethacin.

By adding endothelial cells in suspension to the blood rather than placing the blood on cultured monolayers, we were able to address two issues. First, the possibility that the effect of the monolayers was passive (i.e. covering the plastic surface, to which monocytes may otherwise adhere and become activated) was excluded by observing that endothelial cells in suspension mimicked the activity of monolayers (FIG. 16; n=4). In another experiment, endothelial cells were seeded onto gelatin microcarrier beads, and a similar inhibitory effect was observed, which was not seen with beads without endothelial cells (data not shown). Second, HUVECs in suspension could be added in varying concentrations, allowing the relative proportions of endothelial cells to blood cells to more closely approximate those found in the microcirculation. TNF production was inhibited in a concentration-dependent manner (FIG. 16); TNF release was reduced 60% with the highest concentration of cells tested.

EXAMPLE 11

*E. coli* Stimulating TNF Release

Figure 17:
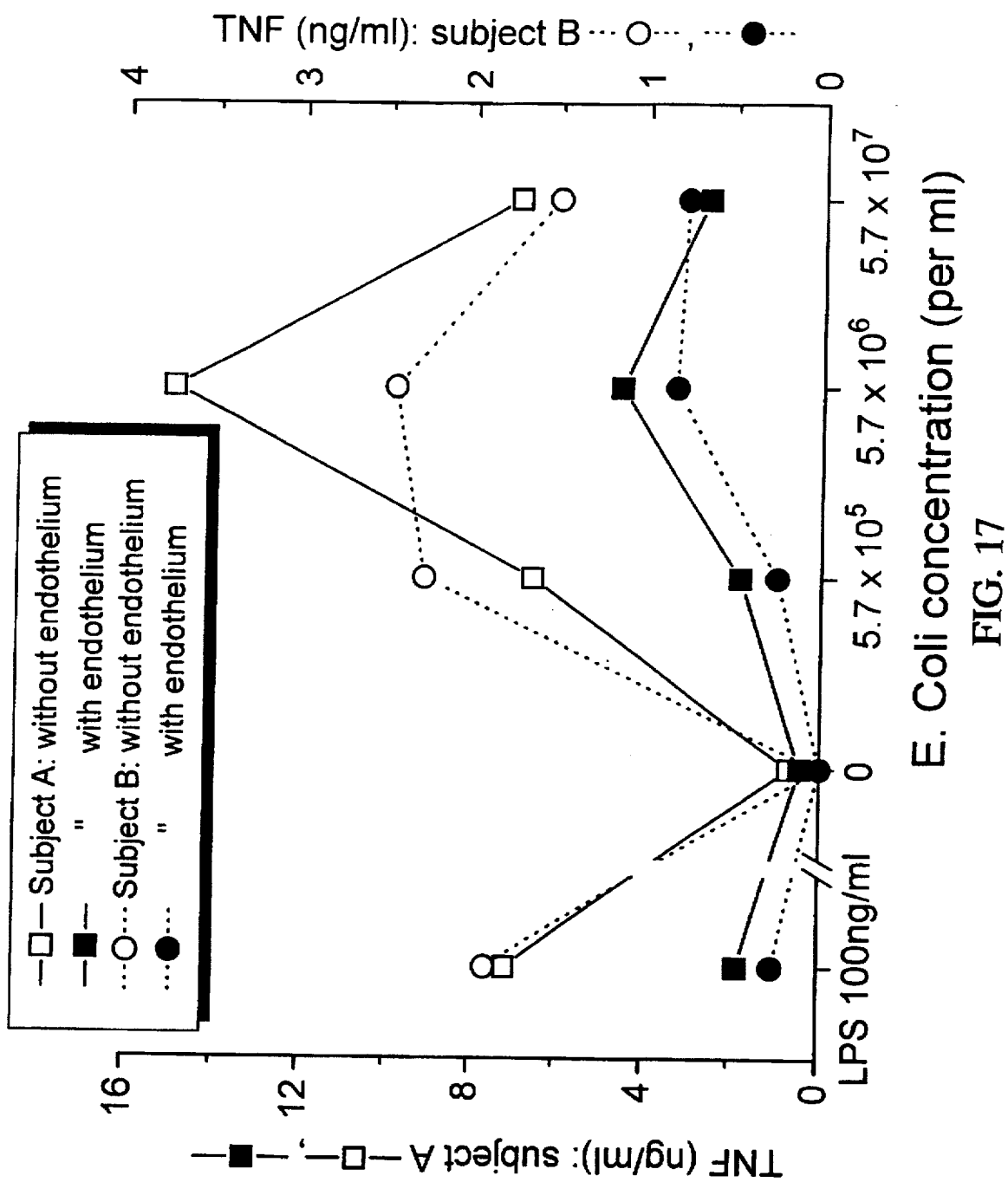
FIG. 17 is a graph depicting the effect of endothelium on TNF release in whole blood in response to E. coli.

Whole gentamicin-killed *E. coli* were examined as another stimulus that probably evokes TNF release by several different pathways; for example, they serve as a phagocytic stimulus and also activate complement components. A single colony of *E. coli* serotype B7 086a61 (ATCC#33985) on an LB plate was cultured overnight in LB Medium (Difco, Detroit, Mich.). The next morning the cells were washed three times in Hanks balanced salt solution (HBSS) and then resuspended in HBSS to $5.7 \times 10^9$ cells per ml. Before addition to blood, bacteria were killed by treatment with gentamicin sulfate (Elkins-Sinn, Cherry Hill, N.J.), 500 μg/ml for one hour. TNF release assays were performed according to procedures given in Example 2. TNF production in whole blood in response to *E. coli* was dose-dependent and greater than that evoked by LPS; furthermore, whereas the response to LPS was dose-dependently antagonized by Polymyxin B, the response to *E. coli* was unaffected (data not shown), indicating that endotoxin is probably not the principal mediator of the response to *E. coli*. TNF release in response to *E. coli* was also markedly inhibited in the presence of endothelium (FIG. 17).

EXAMPLE 12

Prostaglandin and Nitric Oxide Inhibitors

TNF release assays were performed according to procedures given in Example 2.

Endothelial cells were treated with inhibitors of enzymes responsible for production of prostaglandins and nitric oxide. In each case, endothelial cells were pretreated by addition of the inhibitor to the culture medium for one hour, before the addition of blood and the TNF-provoking agonist (e.g., LPS) to the wells. Acetylsalicylic acid (ASA, aspirin), (Sigma, St. Louis, Mo.), which is an irreversible inhibitor of the cyclooxygenase enzyme, was removed after the incubation by washing the endothelial cells three times with Hanks balanced salt solution (HBSS) before adding the blood. Indomethacin and $N^G$-nitro-L-arginine methyl ester (L-NAME; Sigma), which are competitive inhibitors of cyclooxygenase, and nitric oxide synthase, respectively, were added to the HBSS wash solution and again directly to the blood as soon as it had been pipetted into the wells, so that the target enzyme would have no opportunity to escape inhibition. With indomethacin (which has been reported to increase TNF release from macrophages by blocking autocrine production of $PGE_2$), controls were run in which indomethacin was added to the blood in the absence of endothelium.

Figure 18:
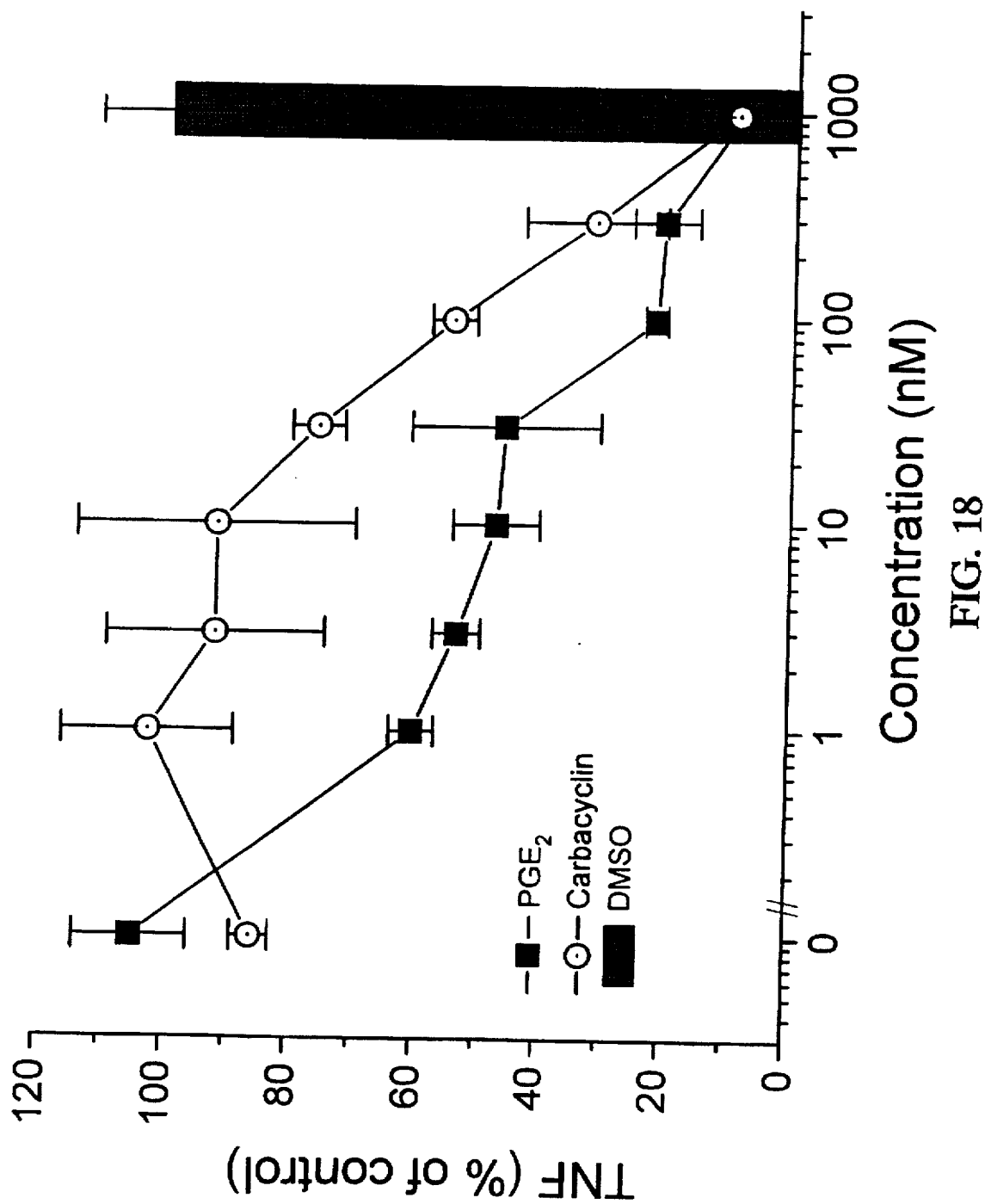
FIG. 18 is a graph depicting inhibition of LPS-induced TNF release in whole blood in response to prostaglandins.
Figure 19:
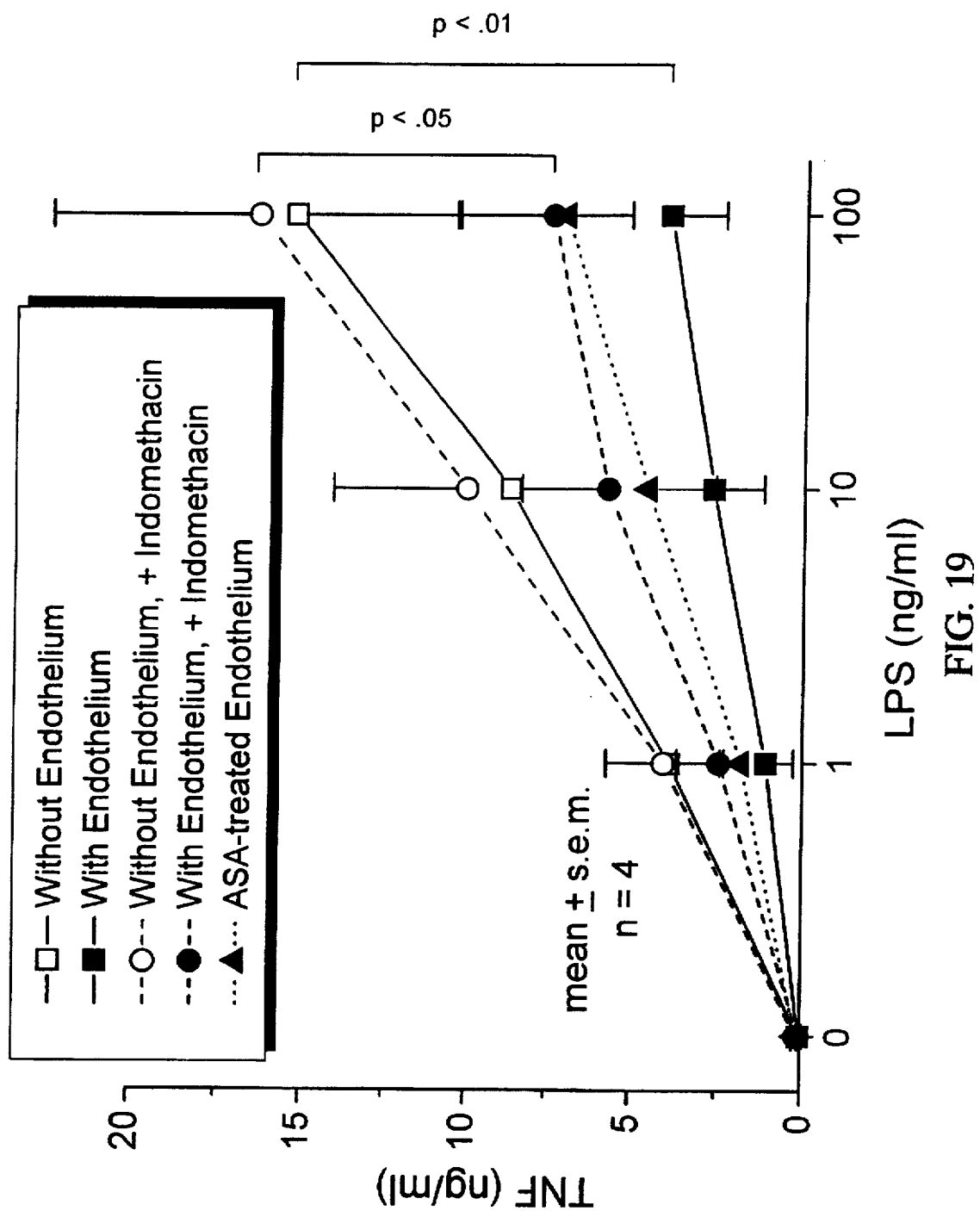
FIG. 19 is a graph depicting the effect of indomethacin or aspirin on endothelial inhibition of LPS-induced TNF release in whole blood.

Authentic $PGE_2$ and carbacyclin (a stable prostacyclin analogue) when added directly to whole blood in the absence of endothelial cells evoked a dose-dependent inhibition of LPS-induced TNF release, with almost complete suppression by either agonist at a concentration of $10^{-6}M$ (FIG. 18). $PGE_2$ was at least 10-fold more potent that carbacyclin. This observation suggested that the effect of the endothelial monolayers may be due to the release of inhibitory prostanoids. Therefore, endothelial monolayers were treated with ASA ($10^{-4}M$ for 1 hour), an irreversible cyclooxygenase inhibitor. ASA attenuated the inhibitory activity, but by less than 40% of the total inhibition. ASA-treated endothelial cells still significantly inhibited TNF release from whole blood (FIG. 12). This dose of ASA reduced the release from cultured HUVECs of prostacyclin (from 4.0 to 0.26 nM) and of $PGE_2$ ((from 0.93 to <<0.2 nM, the limit of detection using a competitive enzyme immunoassay technique (Cayman Chemical, Ann Arbor, Mich.)), and this inhibition persisted for at least two hours. However, a small amount of prostaglandin synthesis recovers after three to four hours, especially when endothelial cells are exposed to LPS (data not shown), which likely reflects induced synthesis of new cyclooxygenase enzyme by the endothelial cells. It seems unlikely that this small amount of prostaglandin, to which the blood cells would not be exposed until at least several hours after activation with LPS, would be capable of eliciting the inhibition observed with the ASA-treated monolayer. Nonetheless, a second set of experiments was performed using indomethacin, another cyclooxygenase inhibitor, taking care that the endothelial cells would remain in contact with it throughout the experiment. In the presence of indomethacin, the wells with endothelium produced significantly less TNF in response to LPS than control wells without endothelium (FIG. 19; n=4). The degree of inhibition was nearly identical to that evoked by ASA-treated endothelial cells. In the absence of endothelium, indomethacin caused marginally higher TNF release with LPS, perhaps by inhibiting production of $PGE_2$ by the monocytes. In the experiment with endothelial cells in suspension, indomethacin caused a modest elevation of TNF release for all concentrations of endothelial cells, but did not block their inhibitory effect (FIG. 16).

Figure 20:
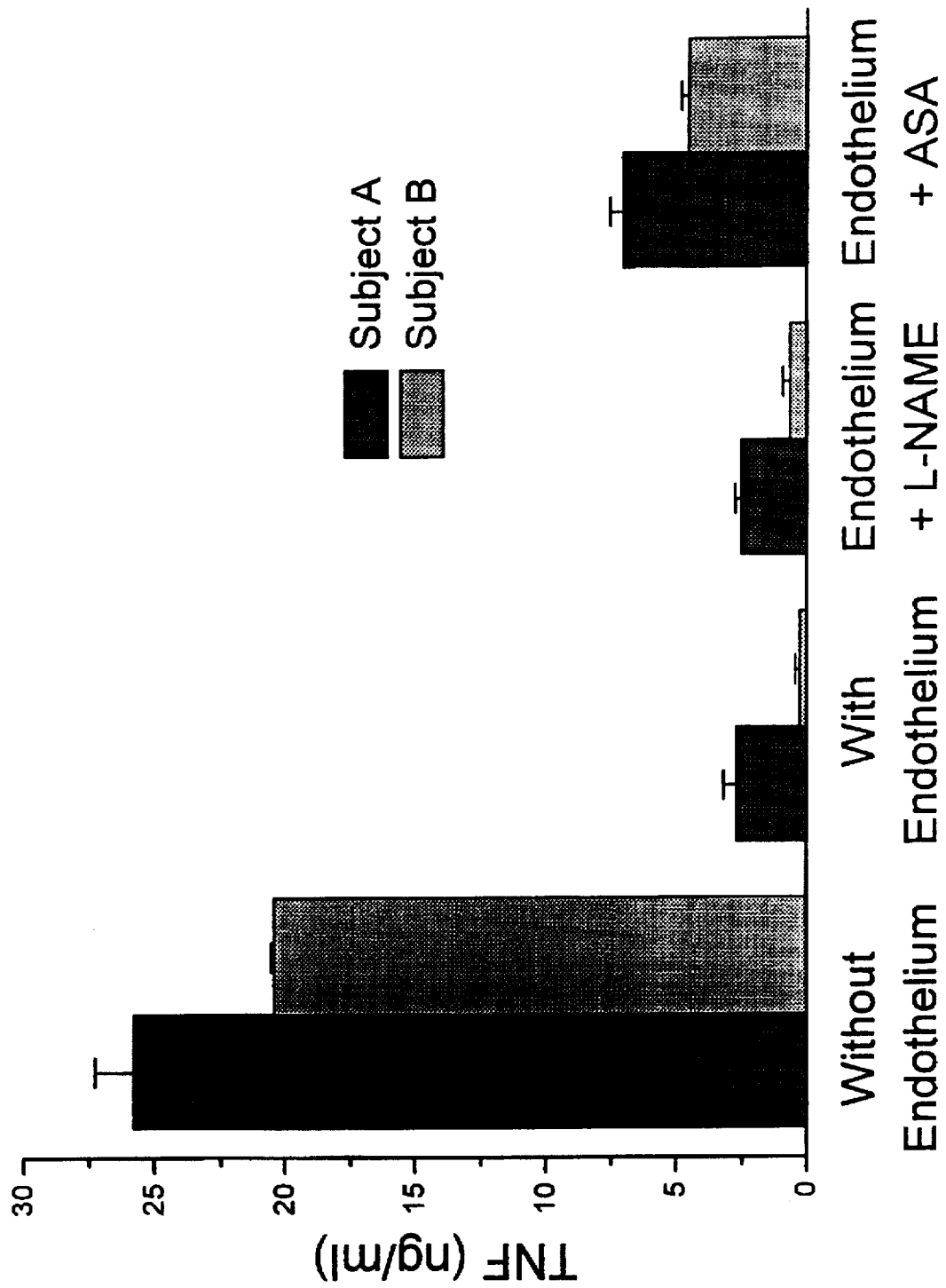
FIG. 20 is a graph depicting the effect of the nitric oxide synthase inhibitor, $N^G$-nitro-L-arginine methyl ester (L-NAME), on endothelial inhibition of LPS-induced TNF release in whole blood.

In order to assess the possibility that the inhibitory activity of endothelial cells was due to their release of nitric oxide (endothelium-derived relaxing factor), a selective inhibitor of nitric oxide synthase, L-NAME ($10^{-4}M$), was used. No reduction of the endothelial inhibition of TNF release was observed (FIG. 20) even if the endothelial cells were incubated with the L-NAME for one hour beforehand. In the same experiments, the partial inhibitory effect of ASA described above was observed.

EXAMPLE 13

Mononuclear Cell Preparations

To establish whether the inhibitory effect of the endothelium was exerted directly on monocytes or required an intermediary blood cell, human peripheral blood mononuclear cells (PBMC) were prepared from freshly drawn heparinized blood by density-gradient separation on Ficoll-Hypaque (Mono-Poly Resolving Medium, Flow Laboratories, McLean, Va.). Furmaniak-Kazmierczak, et al., "Protein S enhances C4b binding protein interaction with neutrophil." *Blood* 81:405–411 (1993). Isolated PBMC were washed three times with RPMI 1640 (Mediatech) and resuspended at a concentration of $3-5\times10^6$ cells/mL. 200 µl aliquots were added to 24-well tissue culture plates, incubated, and assayed as described with whole blood.

The human monocytic cell line, THP-1, was obtained from the American Type Culture Collection (ATCC, Rockville, Md.) and cultured in RPMI 1640 supplemented with 10% (v/v) fetal bovine serum (FBS, Hyclone), 2 mM L-glutamine, 50 IU/ml penicillin, and 50 µg/ml streptomycin (Mediatech). THP-1 cells were washed, resuspended, and used as described for PBMC.

Mononuclear cells ($4.47\pm0.94\times10^6$/ml) isolated from fresh whole blood released TNF dose-dependently in response to LPS in a manner similar to whole blood. Incubation of these cells on an endothelial monolayer slightly inhibited TNF production in response to 100 ng/ml LPS (by 17.7±6.3%, n=8, p<0.05). TNF production by these cells was also less sensitive to inhibition by exogenous $PGE_2$ ($10^{-7}M$): 63.9±9.6% inhibition of isolated PBMCs (n=4) vs. 83.6±2.7% inhibition of whole-blood TNF production (n=12; p<0.05).

THP-1 cells, a human monocytic cell line, cultured at a concentration of $2.3\pm0.7\times10^6$ cells/ml, released TNF dose-dependently in response to a 4-hour incubation with LPS. With 100 ng/ml LPS, they released $4.5\pm0.9$ ng TNF/ml/$10^6$ cells; this response was inhibited 31±14% by incubation on an endothelial monolayer (n=5, p<0.10).

EXAMPLE 14

Pig Aorta in situ

To exclude the possibility that the inhibitory activity of endothelial monolayers was merely an artifact of tissue culture, experiments were performed using intact endothelium in situ in segments of porcine aorta. Normal farm pigs (Spotted Polland) weighing 30–35 kg were euthanized with pentobarbital and the thoracoabdominal aorta removed aseptically. The harvested aorta was rinsed in HBSS containing penicillin 50 IU/ml and streptomycin 50 µg/ml. The aorta was then opened longitudinally along its dorsal surface. The endothelial cell surface was left intact, or denuded mechanically by scraping gently ten times with a metal spatula. The opened aorta was then clamped into a multi-well plexiglass template device, such that the intimal surface of the aorta formed the bottom of the well. The wells were washed with HBSS and blood added and processed exactly as above for 24 well plates.

After the completion of blood incubation, the aortas were removed from the template device and the areas corresponding to the bottoms of the wells were carefully cut out. These were fixed in 2.5% glutaraldehyde, serially dehydrated in ethanol, then subjected to critical-point drying under $CO_2$ (Emscope CPD 750). The segments were then sputter-coated with gold (Balzers MED 010) and imaged in a scanning microscope (JEOL 6400).

Figure 21:
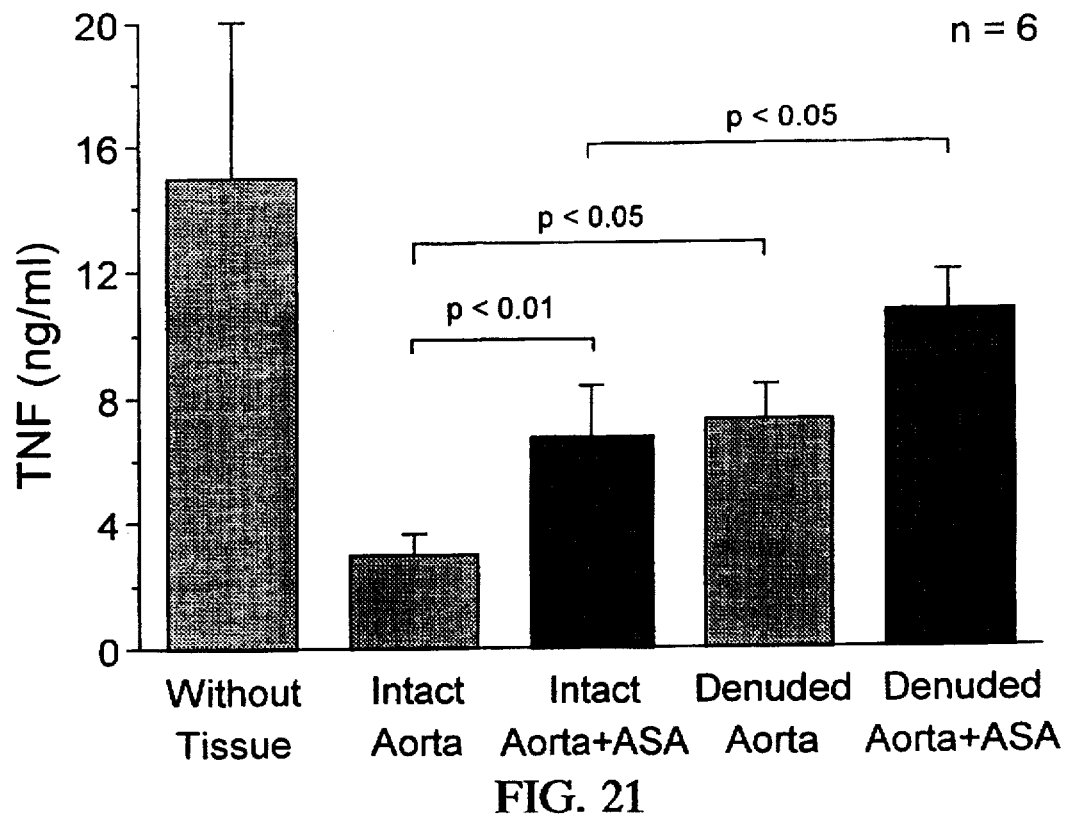
FIG. 21 is a graph depicting the effect of intact or endothelially-denuded pig aorta on TNF release in whole blood.
Figure 22:
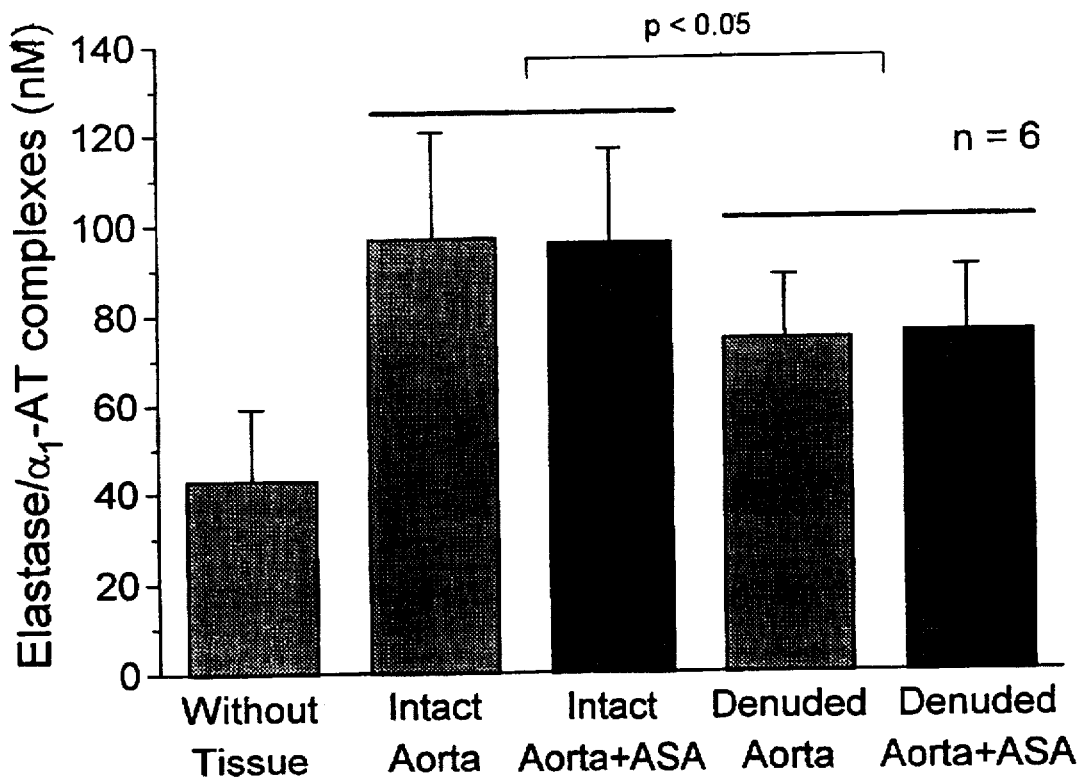
FIG. 22 is a graph depicting the effect of intact or endothelially-denuded pig aorta on elastase release in whole blood.

As with cultured endothelial cells, TNF release was inhibited when whole blood was incubated in the presence of an intact aortic endothelial surface as compared to an adjacent mechanically denuded segment of vessel (FIG. 21;

n=6). Again, ASA pretreatment of the vessel wall partially reduced the inhibitory activity of the endothelium, but the inhibitory effect of ASA-treated endothelial segments (as compared to ASA-treated denuded segments) remained significant. As given in FIG. 22 (n=6), increased elastase release was obtained with both intact aortic endothelium and denuded aortic segment; however, the intact aortic endothelium effect was significantly higher than that obtained with denuded aortic segment. Moreover, ASA pretreatment did not significantly alter the stimulatory effect of either the intact aortic endothelium or the denuded aortic segment on elastase release.

EXAMPLE 15

TNF-inhibitory Activity of HUVEC Conditioned Media

The possibility that the inhibitory effect of the endothelium was mediated by a stable protein factor was examined by fractionating conditioned media. Endothelial cells were grown to confluency as described above. Approximately 2 $m^2$ of cells were washed twice with Hanks balanced salt solution (HBSS) and then placed in 3.3 liters of Medium 199 without supplements. After 24 hours incubation, the conditioned medium was poured off and concentrated on a 3000 MW cut-off membrane (Amicon S1Y3, Beverly, Mass.). This material was further concentrated on a Centriprep 3 concentrator (Amicon), yielding a final volume of ~6 ml. 5 ml of this material was then loaded on a 1.5×100 cm Sephacryl S-100HR gel filtration column and eluted in TBS at 8 ml/hr, collecting 2 ml fractions; fractions were assayed at 1:10 dilution in whole blood for ability to inhibit TNF release as described above.

Figure 23:
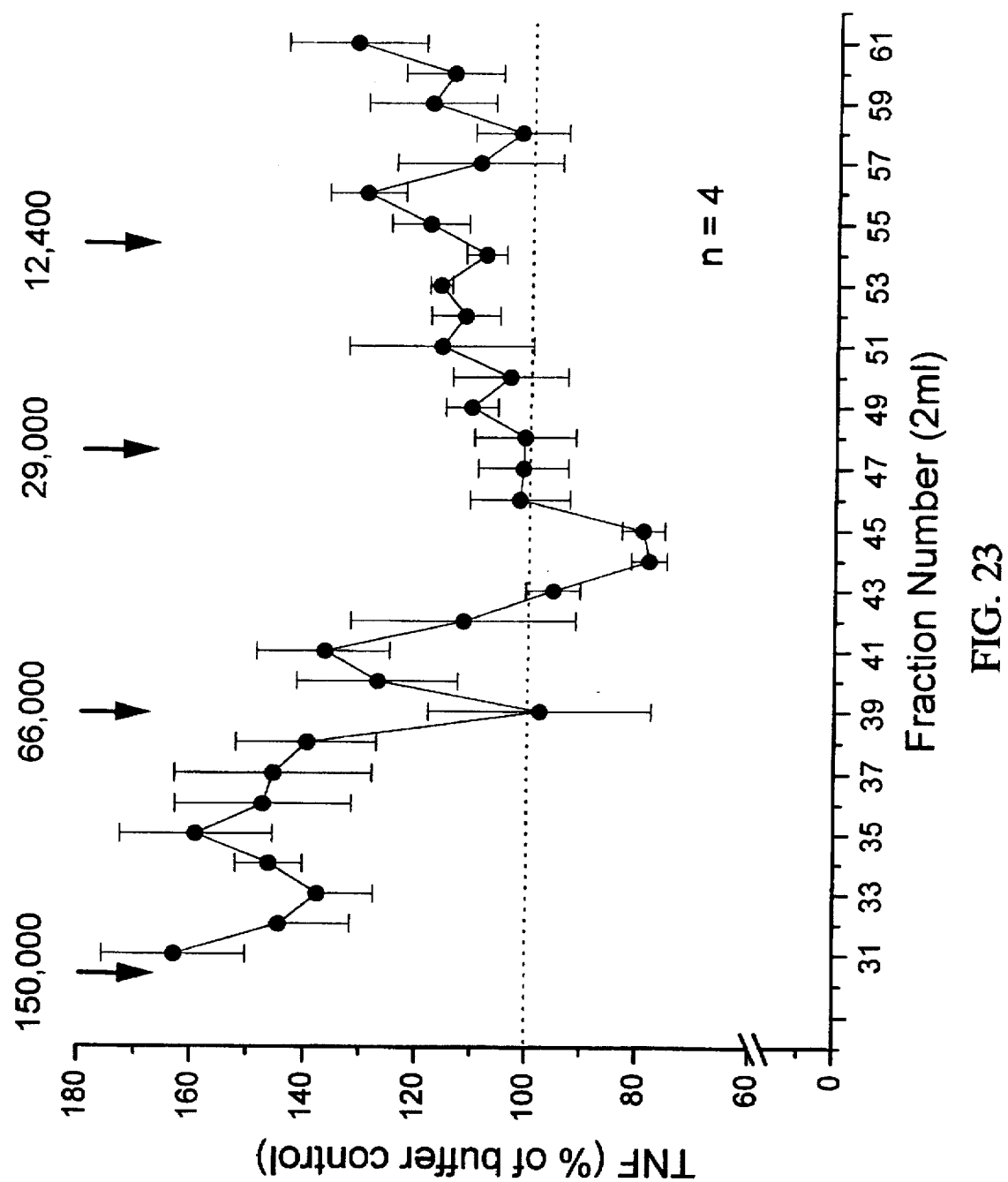
FIG. 23 is a graph depicting TNF-inhibitory activity of fractions separated by gel filtration chromatography of concentrated conditioned media from endothelial cells.

Conditioned medium taken directly from cultured endothelial cells was not found to inhibit TNF release when added 1:10 to blood in the usual assay (data not shown). However, if the endothelial cells release an inhibitory factor into the media, it would be much more diluted in this assay than if it were released directly into the blood from endothelial cells. Therefore, the conditioned medium was assayed after concentration. After the first stage (approximately 66-fold reduction in volume), the conditioned medium was able to inhibit TNF release (by 43%, n=2) but gel-filtered fractions showed no convincing activity. The medium was therefore concentrated a further 7.7-fold and gel filtered; fractions 44 and 45 possessed significant inhibitory activity, corresponding to an estimated molecular weight of ~38 kD by comparison with standards (FIG. 23; n=4).

EXAMPLE 16

Radiolabeled Calmodulin Binding to Monocytic Cell Lines

Bovine testis calmodulin was purified as described above. The calmodulin thus purified was radiolabeled with $^{125}$Iodine ($^{125}$I) using immobilized glucose oxidase/lactoperoxidase (Enzymobeads, BioRad Lab., Cambridge, Mass.). Human monocytic or myelomonocytic cell lines including THP-1, HL-60, MonoMac-6, and U937 were grown in RPMI 1640 containing 10% supplemented bovine calf serum as in Example 13. These cells were washed once in Hanks balanced salt solution (HBSS) supplemented with 1% (v/v) human serum albumin and 20 mM HEPES, pH 7.5 (HBSS-HSA-HEPES) containing 1 mM EDTA, once in HBSS-HSA-HEPES with calcium and magnesium and then resuspended in HBSS-HSA-HEPES with calcium and magnesium at a concentration of $1.25 \times 10^8$ cells/ml. 80 μl ($10^7$ cells) were then aliquoted into 1.5 ml siliconized epindorf tubes and 10 μl of HBSS-HSA-HEPES with increasing concentrations of unlabeled calmodulin from $10^{-9}$ to $2 \times 10^{-5}$M final, or 10 μl HBSS-HSA-HEPES containing 10 mM EDTA to determine non-specific binding added. Next, 10 μl of $^{125}$I-calmodulin was added to a final concentration of $5 \times 10^{-9}$M and allowed to incubate for 40 minutes at 4° C. with intermittent vortexing. After the incubation period, the cells binding $^{125}$I-calmodulin were carefully layered over 9:1 dibutylpthalate:apezion oil and centrifuged at 200× g for five minutes in siliconized 400 μl centrifuge tubes. The supernatant containing free $^{125}$I-calmodulin was then sampled for determination of unbound $^{125}$I-calmodulin and the tip of the centrifuge tube containing the cell pellet amputated and counted in a gamma counter for the determination of bound $^{125}$I-calmodulin. The Ligand (Elsevier) computer software program was then used to calculate a Kd and number of binding sites per cell.

Figure 24:
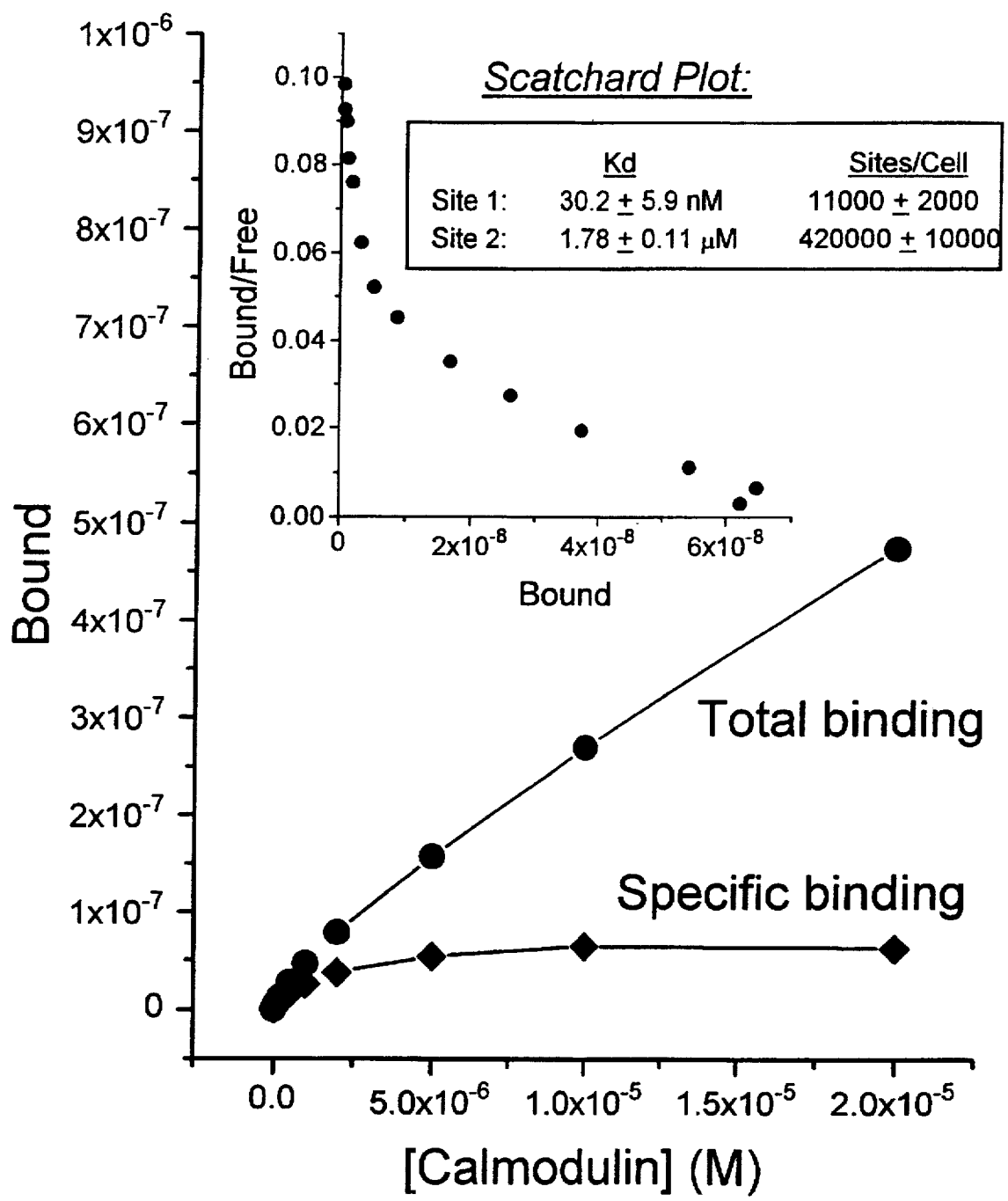
FIG. 24 is a graph demonstrating the binding of $^{125}$I-calmodulin to the THP-1 monocytic cell line.

Two classes of binding sites were identified as shown in Table 4. FIG. 24 depicts the $^{125}$I-calmodulin binding to THP-1 cells which demonstrated a high affinity site with a Kd of about 30 nM and 11,000 sites per cell. This high affinity site was not seen on MonoMac-6 cells. It is presumed to be the calmodulin receptor which mediates the inhibition of TNF and augmentation of elastase release, since its affinity agrees closely with the half maximal biological activity of calmodulin for both TNF and elastase of 30 nM.

TABLE 4

| BINDING OF $^{125}$I-CALMODULIN TO MONOCYTIC CELL LINES | | |
|---|---|---|
| | Kd | Sites/Cell |
| THP-1 Cells | | |
| Site 1 | 30.2 +/− 5.9 nM | 11,000 +/− 2,000 |
| Site 2 | 1.78 +/− 0.11 μM | 420,000 +/− 10,000 |
| HL-60 Cells | | |
| Site 1 | 29.8 +/− 9.7 nM | 7,920 +/− 2,900 |
| Site 2 | 2.36 +/− 0.20 μM | 353,000 +/− 13,000 |
| U937 Cells | | |
| Site 1 | 20.2 +/− 10.4 nM | 3,020 +/− 1,150 |
| Site 2 | 1.84 +/− 0.58 μM | 56,600 +/− 7,600 |
| MonoMac-6 Cells | | |
| Site 1 | | |
| Site 2 | 12.0 +/− 1.0 μM | 2,410,000 +/− 180,000 |

EXAMPLE 17

Cross linking $^{125}$I-calmodulin to Surface Receptors

Figure 25:
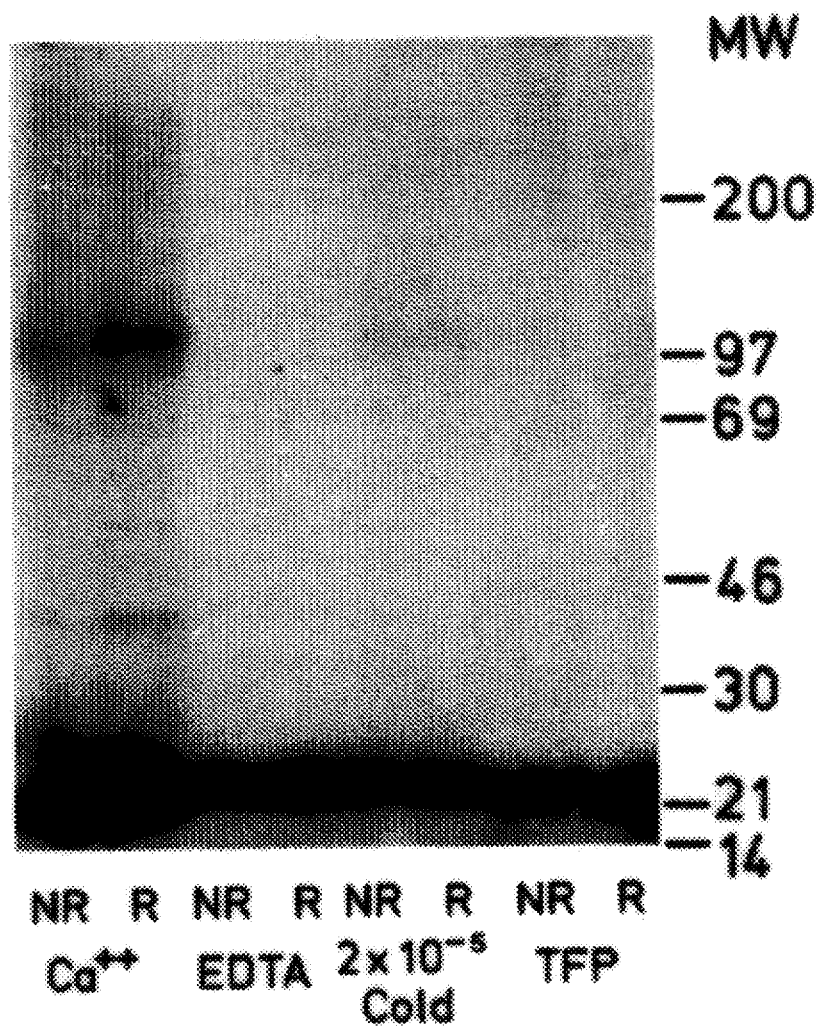
FIG. 25 is an autoradiogram depicting the $^{125}$I-calmodulin-receptor complexes from the THP-1 monocytic cell line.

Calmodulin radiolabeled with $^{125}$I and monocytic cell lines were prepared as described above. For cross-linking, $10^7$ washed cells were suspended in 1 ml Hanks balanced salt solution (HBSS) supplemented with 1% (v/v) human serum albumin and 20 mM HEPES, pH 7.5 (HBSS-HSA-HEPES). Radiolabeled calmodulin was then added in a final concentration of $10^{-7}$M (above Kd for the high affinity site, but below the Kd for the low affinity site) and allowed to bind for 40 minutes. The cross-linking reagent BS$^3$ (Pierce, Rockford, Ill.) dissolved in DMSO was then added in a final concentration of 1 mM and cross linking allowed to proceed for one hour. The unbound and uncross-linked $^{125}$I-calmodulin was then removed by washing twice in HBSS containing 1 mM EDTA. The cell pellet was extracted in extraction buffer consisting of 0.15M NaCl, 0.02M Tris-HCl, pH 7.5, 1% Triton X-100, 0.1 mM PMSF (phenylmethylsulfonyl fluoride), 0.1 mM pepstatin, 0.1 mM leupeptin, 1 mM EDTA, 5 mM benzamidine and 0.02% azide, and allowed to extract overnight at 4° C. with rocking. The next morning the Triton-insoluble material(s) were removed by centrifugation at 14,000 rpm. The Triton solubilized $^{125}$I-calmodulin-receptor complexes were electrophoresed on 10% SDS-PAGE, then fixed to the gel in 40% methanol, 10% acetic acid and the gels dried. The dried gels were exposed to X-OMAT AR film for autoradiography. FIG. 25 is an autoradiograph demonstrating cross-linking of $^{125}$I-calmodulin to THP-1 cells.

Autoradiograms of the $^{125}$I-calmodulin-membrane receptor(s) show two classes of complexes. One complex of apparent molecular weight of 110 kD and a second, less apparent complex of 44 kD. No complexes were observed when $^{125}$I-calmodulin was incubated with the cells in the presence of EDTA, and both complexes were markedly reduced when binding was performed in the presence of excess unlabelled calmodulin. In non-binding cell lines no such complexes were observed after binding and cross-linking.

We claim:

1. A method for treating a patient to inhibit the onset of inflammation, comprising administering to said patient an effective amount of extracellular calmodulin to inhibit production of tumor necrosis factor, whereby inflammation is inhibited.

2. A method for treating a patient for inflammation, comprising administering an effective amount of extracellular calmodulin to relieve said inflammation.

3. A method for treating a patient for conditions attributable to excess release of tumor necrosis factor, comprising administering to said patient an effective amount of extracellular calmodulin to inhibit said excess release of tumor necrosis factor.

* * * * *